(12) United States Patent
Ishitsu et al.

(10) Patent No.: US 7,807,974 B2
(45) Date of Patent: Oct. 5, 2010

(54) NUCLEAR MEDICAL DIAGNOSIS APPARATUS

(75) Inventors: Takafumi Ishitsu, Hitachi (JP); Yuichiro Ueno, Hitachi (JP); Kensuke Amemiya, Hitachinaka (JP); Keiji Kobashi, Mito (JP)

(73) Assignee: Hitachi, Ltd., Tokyo (JP)

( * ) Notice: Subject to any disclaimer, the term of this patent is extended or adjusted under 35 U.S.C. 154(b) by 47 days.

(21) Appl. No.: 12/034,228

(22) Filed: Feb. 20, 2008

(65) Prior Publication Data

US 2008/0210876 A1 Sep. 4, 2008

(51) Int. Cl.
*G01T 1/166* (2006.01)

(52) U.S. Cl. .................. 250/363.04; 250/369; 250/362; 250/363.07

(58) Field of Classification Search ............ 250/363.04, 250/363.07, 363.09, 369, 362
See application file for complete search history.

(56) References Cited

U.S. PATENT DOCUMENTS

| | | | | |
|---|---|---|---|---|
| 5,241,181 A | | 8/1993 | Mertens et al. | |
| 6,635,878 B2 * | | 10/2003 | Bertelsen | 250/369 |
| 7,397,038 B2 * | | 7/2008 | Persyk et al. | 250/370.1 |
| 2003/0047687 A1 * | | 3/2003 | Wollenweber | 250/363.03 |
| 2003/0062482 A1 * | | 4/2003 | Williams et al. | 250/363.03 |
| 2003/0179853 A1 * | | 9/2003 | Amemiya et al. | 378/63 |
| 2005/0067572 A1 | | 3/2005 | Amemiya et al. | |

FOREIGN PATENT DOCUMENTS

| | | |
|---|---|---|
| JP | 2003-255048 | 9/2003 |
| JP | 2003-270350 | 9/2003 |
| JP | 2005-106644 | 4/2005 |
| JP | 2005-106809 | 4/2005 |

\* cited by examiner

*Primary Examiner*—David P Porta
*Assistant Examiner*—Jessica L Eley
(74) *Attorney, Agent, or Firm*—Mattingly & Malur, P.C.

(57) ABSTRACT

A nuclear medical diagnosis apparatus capable of attaining improvement of the sensitivity by the reduction of a count loss of the data is provided. A data sort section inside a data acquisition unit re-arranges and outputs the data packet from a plurality of auxiliary data acquisition unit in order of the detection time data. A coincidence detection section includes a pair check section and a pair generation section. The pair check section refers to a context on the data packet re-arranged in order of the detection time, and judges a pair relating to a coincidence counting. The pair generation section, based on this judgment result, merges the data packet used as a pair, and outputs the same to the collection work station.

5 Claims, 16 Drawing Sheets

NUCLEAR MEDICAL DIAGNOSIS APPARATUS

BACKGROUND OF THE INVENTION

1. Field of the Invention

The present invention relates to nuclear medical diagnosis apparatuses, and in particular, it relates to a nuclear medical diagnosis apparatus such as a PET apparatus and a SPECT apparatus capable of attaining reduction in size of a circuit by simplifying data processing, and at the same time, increasing sensitivity by reducing a count loss of data.

2. Description of the Related Art

A PET (positron emission tomography) apparatus detects the gamma ray emitted from the subject and reconfigures a tomogram showing an accumulated status of the drugs for PET, after or while radiopharmaceutical, which labels a material (for example, glucose, amino acid, and the like) easily accumulatable in the specific area (for example, cancer lesion) of a subject (for example, an examinee) by positron-emitting radionuclide, that is, the drug for PET to a subject, is administered. As the positron-emitting radionuclide, for example, oxygen-15 ($^{15}$O), nitrogen-13 ($^{13}$N), carbon-11 ($^{11}$C), and fluorine-18 ($^{18}$F) are used. As representative drugs for PET, $^{18}$F-fluorodeoxyglucose (18FDG) which accumulates in cancer lesion is known.

The positron-emitting radionuclide contained in the PET pharmaceuticals accumulated in the cancer lesion emits positron. This positron interacts with neighboring electron and annihilates. At this time, a pair of gamma rays (pair annihilation gamma rays) having an energy of 511 keV are emitted from the subject in a direction about 180° opposite, respectively. Consequently, two gamma rays each having an energy of about 511 keV detected approximately at the same time are highly probable to be a pair annihilation gamma rays generated by a single event (pair annihilation of positron and electron). Consequently, based on the position of two radiation detectors (a pair of detectors) separately detecting the two gamma rays that meet these conditions (synchronicity and energy), each track of these gamma rays can be presumed.

Likewise, by collecting the track information on a large number of pair of gamma rays, and based on these pieces of the track information, if the image reconfiguration represented by a filtered back projection (FBP) method is performed, a tomogram representing an internal radiation concentration distribution caused by the positron-emitting radionuclide can be obtained.

To generate a good PET image, it is necessary to specify a pair of detection data corresponding to the pair annihilation of gamma rays for every event. Hence, in the PET apparatus, a coincidence counting circuit specifies a pair of detection data corresponding to the pair of gamma rays practically and simultaneously detected. In this way, the pair annihilation of gamma rays is accurately recognized and used for the generation of the tomogram, and even when they are the diffused gamma ray or the annihilation gamma ray, the detection data which has detected only either one is removed.

When the coincidence counting circuit receives two detection data having time information within a predetermined time window, the coincidence circuit performs a coincidence counting with the detection data taken as received practically at the same time. The time window, for example, is a width of 10 "ns", and is set up as short as possible to avoid accidental coincidence counting in consideration of the tracking time difference between two gamma ray of the pair annihilation of gamma rays, a limitation of the time accuracy of the signal processing system of the apparatus, and the like.

The accidental coincidence counting means that since a plurality of events (for example, an emission of gamma rays) of the same type has happened at the same time, the observational result caused by another event is taken as the observational result caused by the single event, and is erroneously recognized. For example, when two positrons annihilate at the same time in the body and the gamma rays caused by the annihilation of these positrons are detected one by one, a problem arises that it is difficult to judge that this phenomenon is attributable to the accidental coincidence counting.

A SPECT (Single Photon Emission Computed Tomography) examination is an examination that administers an radio-active drugs (drugs for SPECT), which labels a material easily accumulatable in the specific area in a live body by a single photon emission nuclide, to the examinee, and after that (or while administering), detects gamma ray emitted from the examinee, thereby reconfiguring a tomogram showing a collection and distribution status of the drugs for SPECT.

The single photon emission nuclide is broken down with an intrinsic probability by generating an electron capture (EC) and the like, and emits a single photon of the gamma ray. This nuclide includes technetium-99m ($^{99m}$Tc), gallium-68 ($^{68}$Ga), thallium-201 ($^{201}$Tl), and the like. The half-life periods of these nuclides are generally longer than the half-life period of the positron emitting radionuclide used for the PET examination, and for example, are 6.0 days (in case of $^{99m}$Tc), 3.3 days (in case of $^{67}$Ga) or 73 days (in case of $^{201}$Tl), and the like. In the SPECT examination, by providing a collimator for the radiation detector and limiting an incident angle of the gamma ray, the track of the gamma ray is presumed. These single photon emitting nuclides emit the gamma ray having energy of 100 keV order.

The nuclear medical diagnosis apparatus such as the PET apparatus, for example, includes detector units to the extent of 30 units to 100 units (see JP-A-2005-106644). This detector unit packs radiation detectors for every predetermined number for about every several hundreds to several thousands.

The number X of coincidence counting circuits necessary in principle for confirming a combination of all the detector units can be determined by $X=_NC_2$ provided that the number of detector units is taken as N. Consequently, for example, if the detector units provided for the nuclear medical diagnosis apparatus are 100 units, the calculation result of this number X is about 5000. However, in the actual nuclear medical diagnosis apparatus, the coincidence counting circuits need only be about half this number. This is because, due to the geometrical relative position of the two detector units, there are a considerable number of combinations in which the segment connecting these detector units is unable to pass through a subject.

Heretofore, the coincidence between has been performed by using an analogue circuit. In this method, while a circuit scale need only be small, there are a lot of fluctuations in time, and the adjustment thereof has been difficult. Hence, a method of performing the coincidence between by digital circuit has come into practical use. According to this method, based on the timing when a radiation detection signal is received, the detection time is digital-converted to generate detection time data, and by comparing the generated detection time data with each other, the coincidence between is performed. According to this method, the width of the time window relative to the coincidence counting can be easily set up, so that the coincidence counting of higher accuracy can be performed. However, according to this method, the circuit scale of the coincidence detection circuit becomes vast.

Hence, U.S. Pat. No. 5,241,181 specification discloses a Coincidence Detector for a PET Scanner in which, heretofore, the digitalized time signal from each detector unit has been stored in a shift register, and all the combinations have been compared by each comparator circuit, thereby performing the coincidence between.

According to the conventional "Coincidence Detector for a PET Scanner", the signal from each unit is coincidence-judged by a time sharing to attain the reduction of the number of circuits, and the time signal data from each detector unit is stored in a shift register, and the comparison of all the combinations restricted by the position is performed.

However, this "Coincidence Detector for a PET Scanner" can process only one event within a time frame. Hence, to increase the number of units, it is necessary to make the time frame short in order to process a vast amount of data or reduce the number of radiation detectors stored in one unit and reduce the number of events per each unit. However, when the time frame is made short, a rate of the set of data crossing over the time frame increases, and a rate of the data abandoned without being used for the image formation also increases. That is, a count loss of the data increases, and the sensitivity of the apparatus is lowered. When the number of radiation detectors stored in one unit is reduced, it is necessary to increase the number of units in order to obtain the same performance, and therefore, the required coincidence detection circuit is also increased, thereby increasing the circuit scale.

In recent years, to improve the resolution, a degree of integration of the radiation detectors to be disposed is apt to become high. In the apparatus in which the degree of integration of the radiation detectors is made high, a probability is increased that a piece of the radiation ray is diffused, and is detected as a scattered radiation by a plurality of radiation detectors. Thus, heretofore, a technique has been desired in which, by utilizing the data of the scattered radiation which is abandoned as the energy is less than the predetermined value, the sensitivity of the apparatus is improved.

SUMMARY OF THE INVENTION

An object of the present invention is to provide a nuclear medical diagnosis apparatus capable of attaining the improvement of the sensitivity by reducing a count loss of the data.

To solve the problem, a first nuclear medical diagnosis apparatus of the present invention is provided for every radiation detector, and includes a plurality of data generation sections for generating detection data including detection time data respectively based on radiation detection signal outputted from the radiation detector; a detection data output section for outputting the detection data outputted from the plurality of data generation sections in order of the time of the detection time data contained in the detection data; and a coincidence counting device for performing a coincidence counting based on the plurality of detection data outputted in order of the time.

To solve the problem, a second nuclear medical diagnosis apparatus of the present invention includes a plurality of data generation sections for generating detection data including detection time data based on radiation detection signal; a detection data output section for outputting a predetermined number of detection data outputted from the plurality of data generation sections in order of the time of the detection time data contained in the detection data; and a detector scatter restoration process section for performing a detector scatter restoration process based on the plurality of detection data outputted in order of the time.

According to the nuclear medical diagnosis apparatus of the present invention, the improvement of the sensitivity can be attained by reducing a count loss of the data.

Other objects, features, and the advantages of the present invention will become apparent from the following description of the embodiments of the present invention with reference to the accompanying drawings.

DESCRIPTION OF THE INVENTION

First Embodiment

Next, referring to the accompanying drawings, the embodiments of the present invention will be described in detail.

Figure 1:
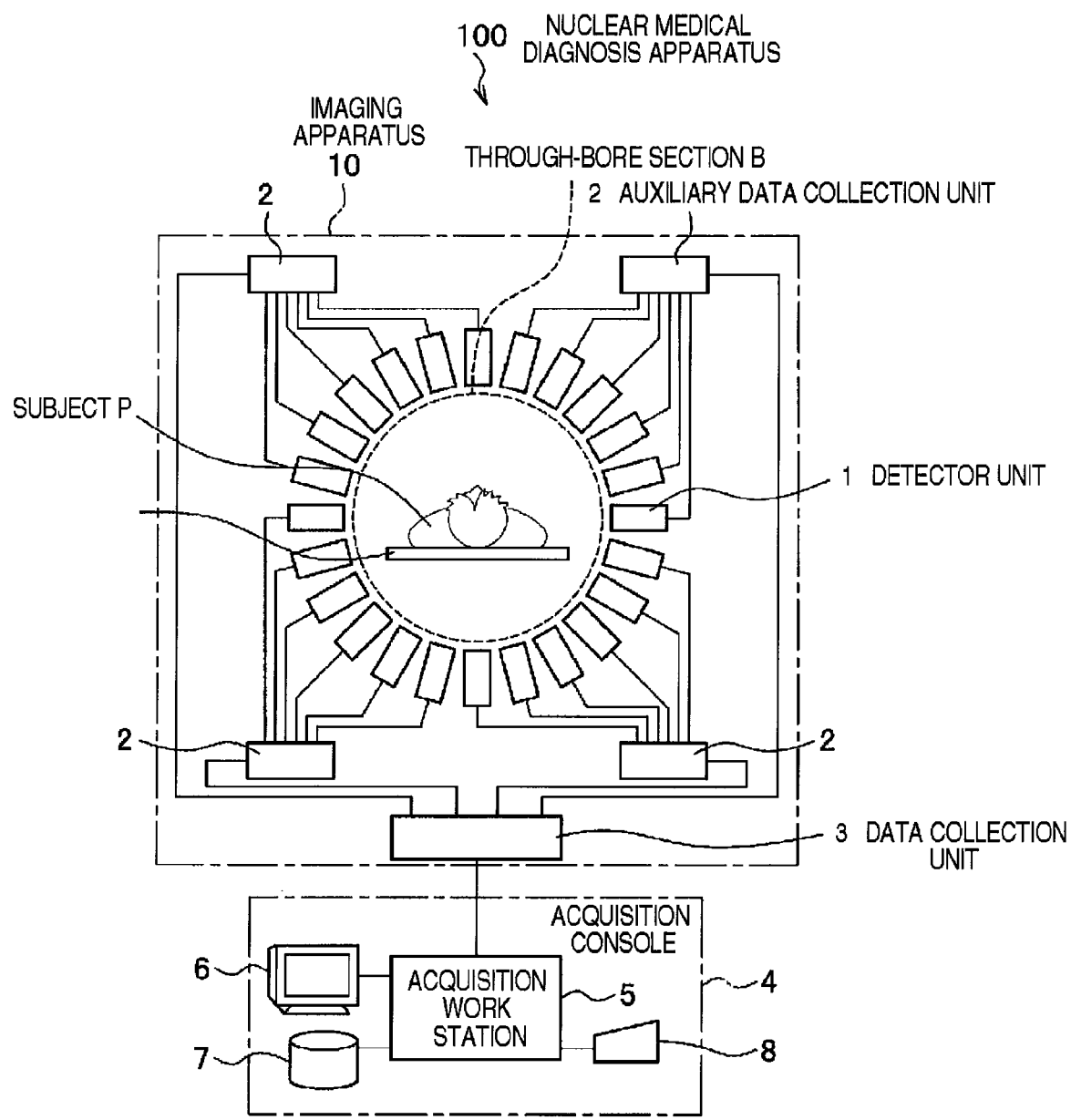
FIG. 1 is a configuration block diagram showing a nuclear medical diagnosis apparatus according to a first embodiment of the present invention.

As shown in FIG. 1, a nuclear medical diagnosis apparatus 100 according to a first embodiment is a PET apparatus (Positron Emission Tomography Apparatus), and includes an imaging apparatus 10, an acquisition console 4, and a bed 11 for supporting a subject P.

The imaging apparatus 10 forms a through-bore section B insertable with a bed 11 loaded with a subject P, and includes a number of detector units 1 circularly disposed surrounding this through-bore section B, a plurality of auxiliary data acquisition units 2, and a data acquisition unit 3. Certain number of the neighboring detector units 1 are connected to one auxiliary data acquisition unit 2, respectively. A plurality of auxiliary data acquisition units 2 are connected to the data acquisition unit 3.

In the present embodiment, a description will be made on the case where the number of the data acquisition unit 3 is one, the number of the auxiliary data acquisition unit 2 is four, and the number of the detector unit 1 is 24. However, these numbers can be increased or decreased more. For example, these numbers are reduced so as to attain the reduction in the circuit scale or the number of detector units 1 is increased so as to improve the resolution or the number of auxiliary data acquisition units 2 is increased so as to disperse the data processing and attain the small scale of each circuit.

In the present embodiment, a hierarchic structure is formed in which signal lines converge in the order of the detector unit 1, the auxiliary data acquisition unit 2, and the data acquisition unit 3. However, for example, a hierarchy having a second auxiliary data acquisition unit (not shown) is provided to connect the detector unit 1, the auxiliary data acquisition unit 2, the second auxiliary data acquisition unit (not shown), and the data acquisition unit 3 in that order, and is multileveled, thereby making it possible to attain the distributed processing and the small scale of the circuit.

The acquisition console 4 includes an collection work station 5 for receiving and processing the data from the data acquisition unit 3, an operating section 8 for inputting the data and instructions into the collection work station 5, a display device 6 for displaying the image and the like generated by the collection work station 5, and a data storage 7 for accumulating the data received or processed by the collection work station 5.

Figure 2:
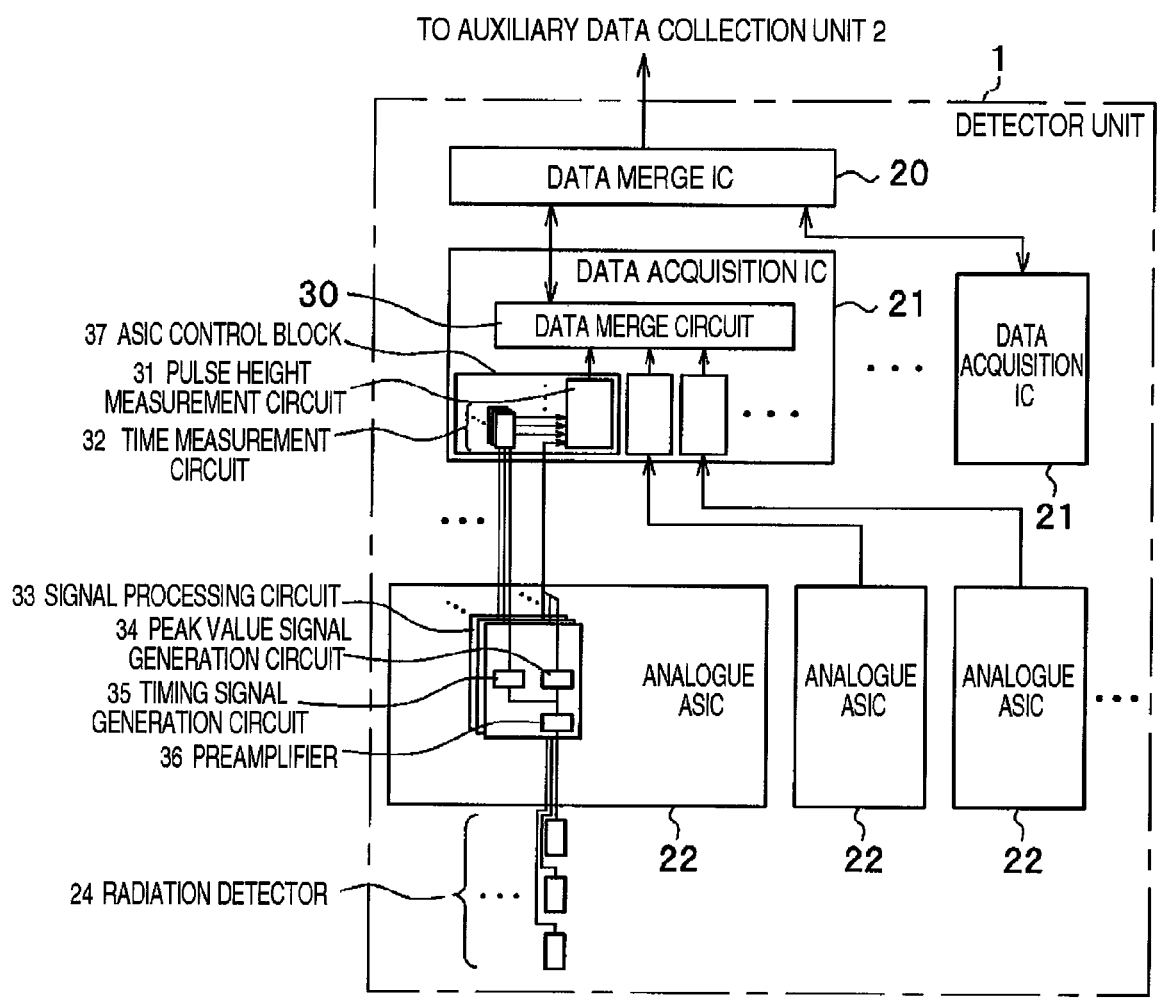
FIG. 2 is a configuration block diagram showing in details a detector unit.

As shown in FIG. 2, the detector unit 1 includes a plurality of radiation detectors (hereinafter, referred to as detector) 24, a plurality of analogue ASIC 22, and a plurality of data acquisition ICs 21 and data merge ICs 20.

The detector 24 is a semiconductor radiation detector. The semiconductor radiation detector, for example, includes a semiconductor material such as cadmium telluride and cadmium zinc telluride, a positive electrode provided on one surface of this semiconductor material, and a negative electrode provided on the other surface of the semiconductor material. The semiconductor material is disposed between the positive electrode and the negative electrode. Between the positive electrode and the negative electrode, a high voltage is applied. When gamma ray is incident on the detector 24, by the action between the semiconductor material and the gamma ray, a pair of electron and hole is generated inside the semiconductor material. The generated electron and hole are collected by the positive electrode and the negative electrode, respectively, and become a gamma ray detection signal which is an electric signal, and is outputted from the detector 24. As the detector 24, a scintillation radiation detector can be also used. The scintillation radiation detector includes a scintillator which generates photon by being excited by gamma rays, and a photoelectron multiplier (or photo diode) which receives the photon and convert it into an electric signal.

The analogue ASIC 22 receives a gamma ray detection signal from the detector 24. The data acquisition IC 21 receives a signal and data (information) outputted from the analogue ASIC 22. The data merge IC 20 merges the data outputted from the data acquisition IC 21, and outputs its data to the auxiliary data acquisition unit 2.

One analogue ASIC 22 includes a plurality of signal processing circuits (signal processors) 33. The output terminal of one detector 24 is connected to the input terminal of one signal processing circuit 33. That is, one signal processing circuit 33 receives the gamma ray detection signal outputted from one detector 24, and processes this gamma ray detection signal. The signal processing circuit 33 includes a preamplifier 36 connected to the detector 24, and a timing signal generation circuit 35 and a pulse height signal generation circuit 34 connected to this preamplifier 36.

The data acquisition IC 21 includes a plurality of ASIC control blocks 37 and a data merge circuit 30. One analogue ASIC 22 is provided with one ASIC control block 37. The plurality of ASIC control blocks 37 is connected to one data merge circuit 30. The ASIC control block 37 includes a plurality of time measurement circuits 32, and one pulse height measurement circuit 31 connected with these time measurement circuits 32. The timing signal generation circuit 35 of one signal processing circuit 33 inside one analogue ASIC 22 is connected to one time measurement circuit 32 of the ASIC control block 37. A pulse height signal generation circuit 34 of the signal processing circuit 33 inside one analogue ASIC 22 is connected to the pulse height measurement circuit 31 of one ASIC control block 37. The data acquisition IC 21, for example, is realized by a FPGA (Field Programmable Gate Array).

Figure 3:
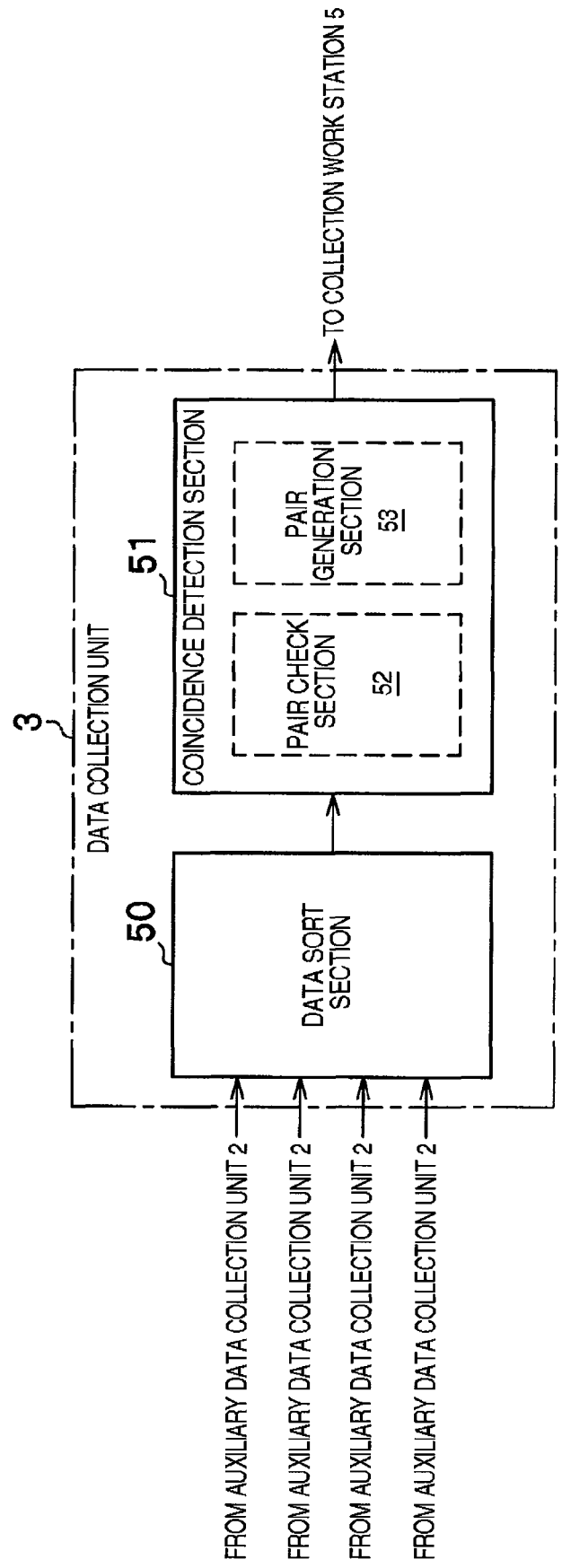
FIG. 3 is a configuration block diagram showing in details a data acquisition unit.

As shown in FIG. 3, the data acquisition unit 3 includes a data sort section 50 and a coincidence detection section (coincidence device) 51. The data sort section 50 is positioned at the input side of the data acquisition unit 3, and the coincidence detection section 51 is positioned at the output side of the data acquisition unit 3. The coincidence detection section 51 includes a pair check section 52 and a pair generation section 53.

Figure 4:
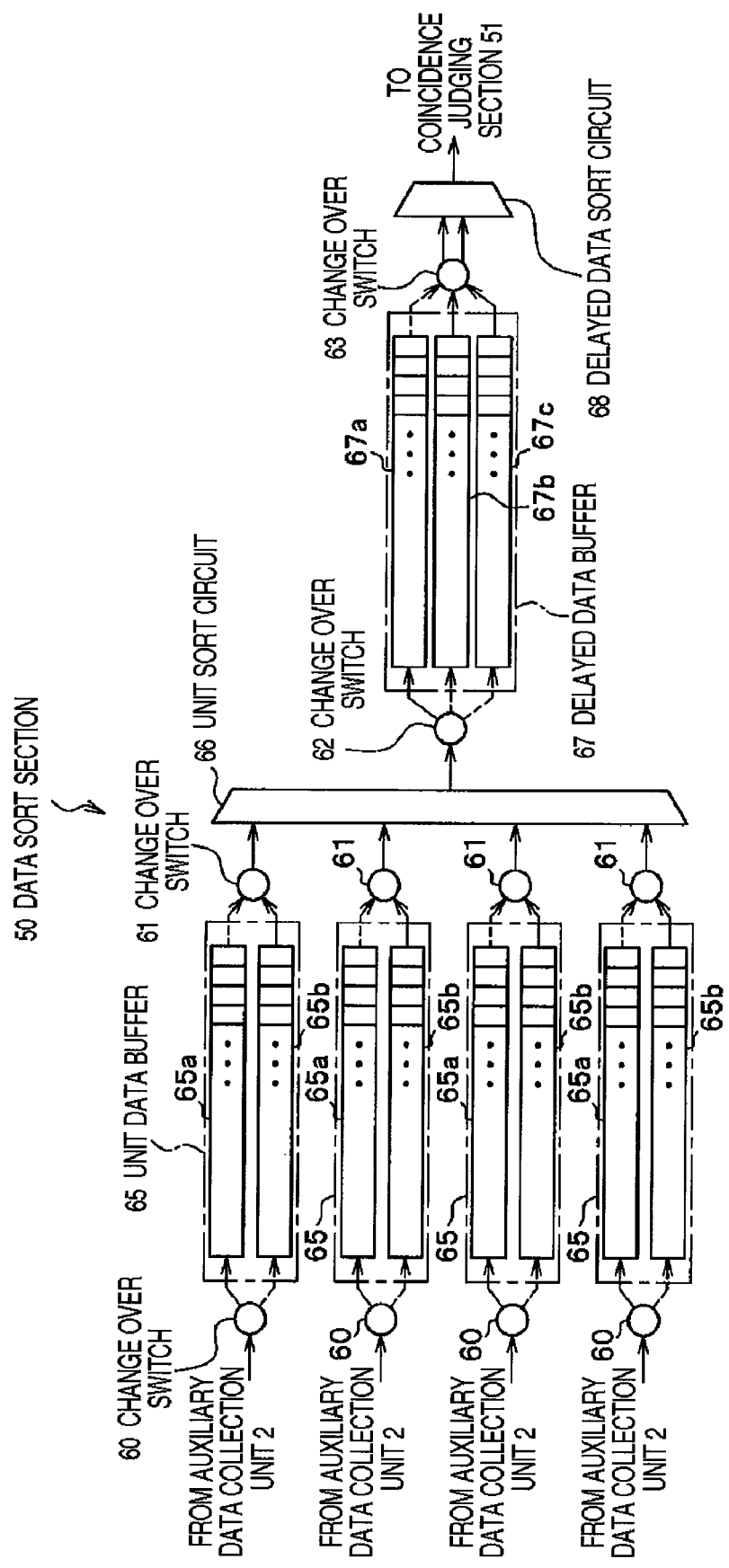
FIG. 4 is a configuration block diagram showing in details a data sort section.

As shown in FIG. 4, the data sort section 50 includes four each change over switches 60 and 61, four unit data buffers 65, a unit sort circuit 66, change over switches 62 and 63, a delayed data buffer 67, and a delayed data sort circuit 68. In the present embodiment, while a description has been made on the case where the number of the auxiliary data acquisition unit 2 (see FIG. 1) is four, the number of auxiliary data acquisition units 2 may be other than four. In this case, each number of change over switches 60 and 61 and unit data buffers 65 is made the same as the number of auxiliary data acquisition units 2.

Each unit data buffer 65 includes two buffers, that is, a first buffer 65a and a second buffer 65b. The delayed data buffer 67 includes three buffers, that is, a first buffer 67a, a second buffer 67b, and a third buffer 67c.

Each change over switch 60 is connected to one each input terminal of the first buffer 65a and the second buffer 65b of one unit data buffer 65. Each change over switch 61 is connected to one each output terminal of the first buffer 65a and a second buffer 65b of one unit data buffer 65. One auxiliary data acquisition unit 2 is connected to one of the first buffer 65a and the second buffer 65b of one unit data buffer 65 by the change over operation of the relevant change over switch 60. The unit sort circuit 66 is connected to one of the first buffer 65a and the second buffer 65b of one unit data buffer 65 by the change over operation of the relevant change over switch 61.

The unit sort circuit 66 is connected to two buffers from among a first buffer 67a, a second buffer 67b, and a third buffer 67c by the change over operation of the change over switch 62. The two buffers from among the first buffer 67a, the second buffer 67b, and the third buffer 67c are connected to a delayed data sort circuit 68 by the change over operation of the change over switch 63.

Figure 5:
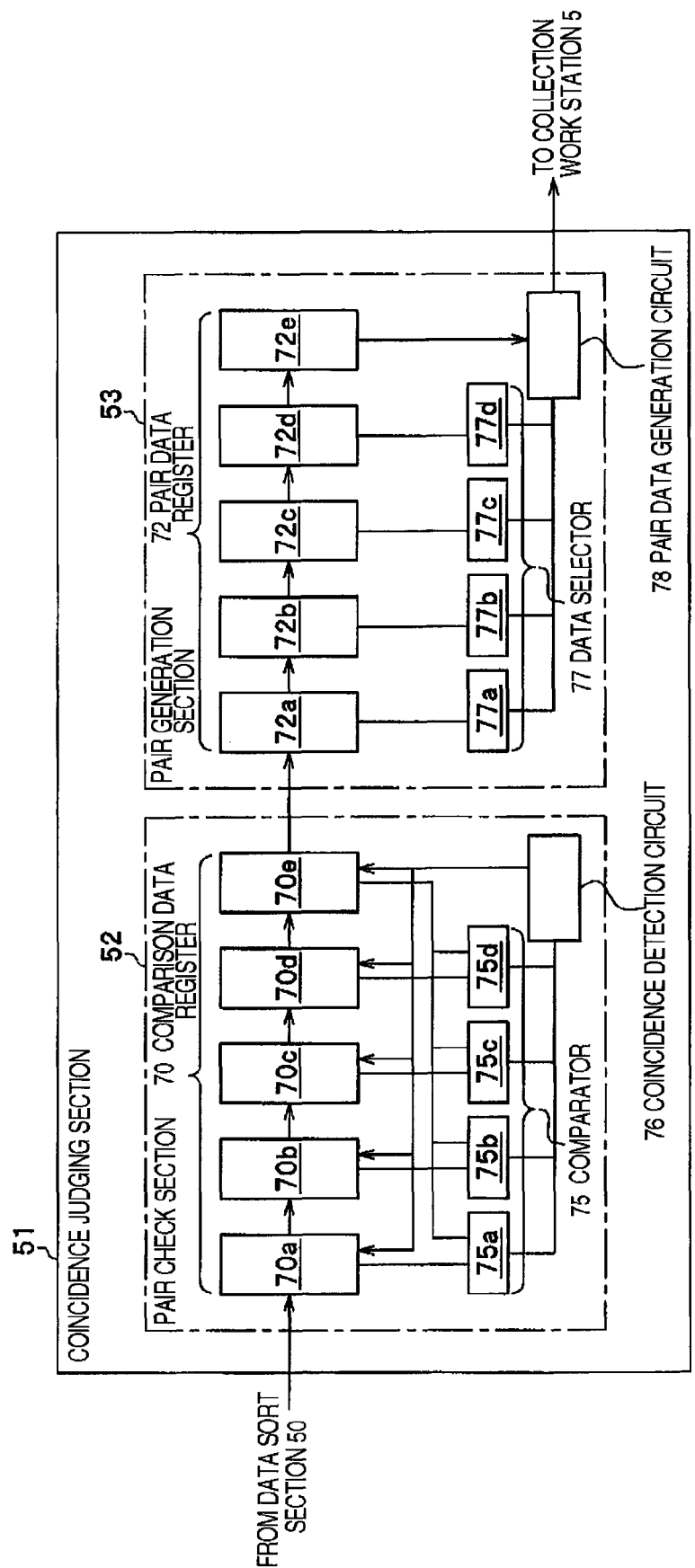
FIG. 5 is a configuration block diagram showing in details a coincidence counting section.
Figure 6:
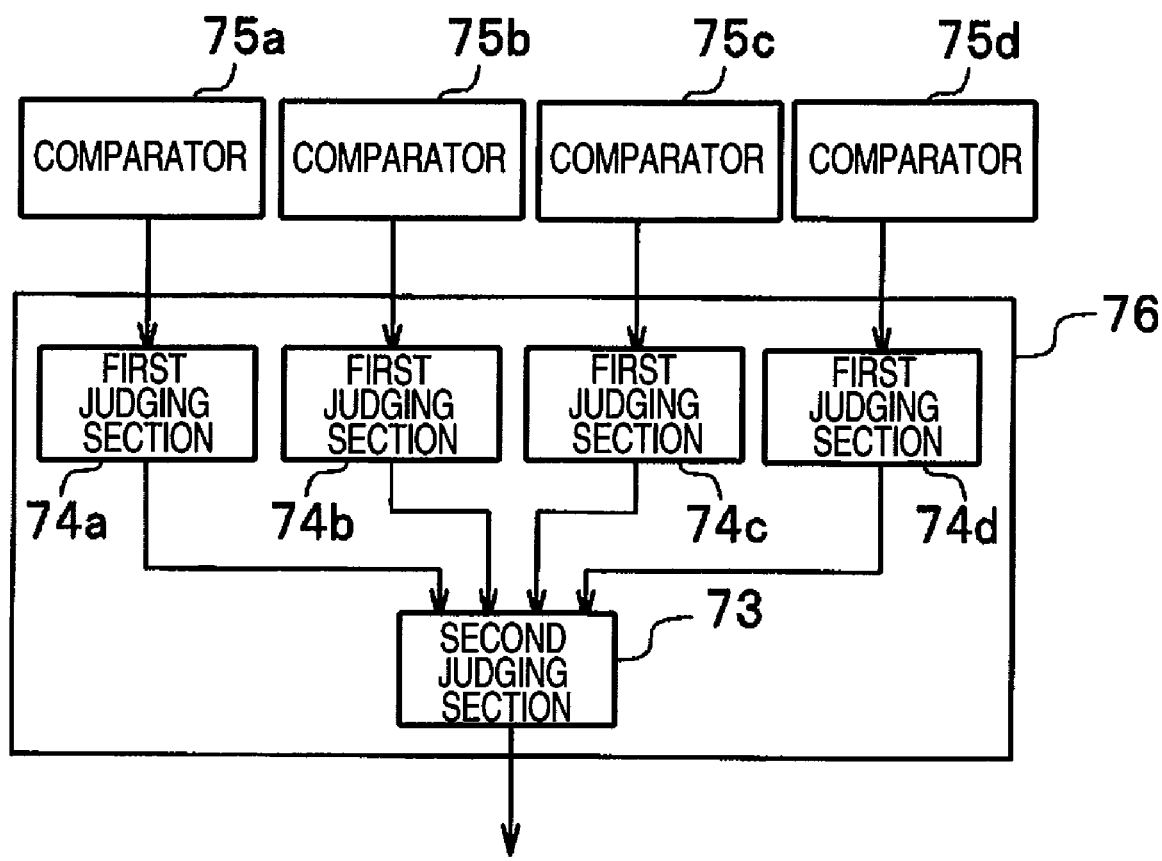
FIG. 6 is a block diagram showing in details a coincidence detection circuit.

As shown in FIG. 5, the pair check section 52 includes a comparison data register 70 including registers 70a to 70e connected in series, a comparator 75 including comparators 75a to 75d, and a coincidence detection circuit 76. The comparison data register 70 is a shift register connecting in series the registers 70a to 70e from the input terminal (register 70a) of the coincidence detection section 51 to the output terminal (register 72e) (that is, forward direction) of the coincidence detection section 51, and allows the data stored in the registers 70a to 70e to be shifted to the next register in the forward direction every one clock. A register 70a is connected to the output terminal of the data sort section 50, that is, the delayed data sort circuit 68. A comparator 75a is connected to the registers 70a and 70e. Likewise, a comparator 75b is connected to registers 70b and 70e, and a comparator 75c is connected to the registers 70c and 70e, and a comparator 75d is connected to the registers 70d and 70e. The coincidence detection circuit 76, as shown in FIG. 6, has first judging sections (coincidence counting sections) 74a to 74d and a second judging section 73. The first judging section 74a is connected to the comparator 75a, the first judging section 74b to the comparator 75b, the first judging section 74c to the comparator 75c, and the first judging section 74d to the comparator 75d. The second judging section 73 has the output terminal connected to the registers 70a to 70e, and has the input terminal to the first judging section 74a to 74d, respectively.

The pair generation section 53 includes a pair data register 72 including registers 72a to 72e connected in series, a data selector 77 including a plurality of selectors 77a to 77d, and a pair data generation circuit 78. The pair data register 72 is a shift register, and allows the data stored in the registers 72a to 70e to be shifted to the next register in the forward direction every one clock. The register 72a positioned at the input terminal of the pair data register 72 is connected to the register 70e positioned at the output terminal of the pair check section 52. The register 72e positioned at the output terminal of the pair data register 72 is connected to a pair data generation circuit 78. The data selector 77a connected to the register 72a, the data selector 77b connected to the register 72b, the data selector 77c connected to the register 72c, and the data selector 77d connected to the register 72d are connected to the pair data generation circuit 78. The pair data generation circuit 78 is connected to the collection work station 5.

Referring back to FIG. 1, to perform the PET examination by using the nuclear medical diagnosis apparatus 100, the bed 11 holding a subject P administered with the drugs for PET in advance is inserted into the through-bore section B. When the drugs for PET labeled by the positron-emitting radionuclide having an extremely short half-life period (for example, $^{15}$O) are used, the examination is performed, while administering the drugs for PET.

After a subject P is inserted into the through-bore section B, a doctor (or a radiological technician) inputs an examination start instruction from an operating section 8. By the examination start instruction outputted from the operating section 8, a switch (not shown) is switched on, and from a power source (not shown), a voltage is applied to each circuit included in the detector 24, the analogue ASIC 22, and a plurality of data acquisition ICs 21 and data merge ICs 20. Prior to the insertion of the subject P into the through-bore section B, by the input of the examination start instruction from the operating section 8, the voltage may be applied to the detector 24 and the like. Each detector 24 detects the gamma ray emitted from the subject P caused by the drugs for PET accumulated in the cancer lesion, and outputs a gamma ray detection signal. The gamma ray detection signal outputted from the detector 24 is received at the corresponding preamplifier 36.

The preamplifier 36 amplifies the gamma ray detection signal. The gamma ray detection signal outputted from the detector 24 is extremely feeble, and therefore, the preamplifier 36 to be used, for example, is a low noise charge integration type. The preamplifier 36 outputs an amplified gamma ray detection signal to the pulse height signal generation circuit 34 and the timing signal generation circuit 35.

The pulse height signal generation circuit 34, based on the amplified gamma ray detection signal, generates and outputs a pulse height signal representing the energy of the gamma ray detected by the detector 24. This pulse height signal is a signal representing the energy of the detected radiation by an analogue value (for example, the potential of this signal). The pulse height signal generation circuit 34 includes a band pass filter (not shown), and by filtering the received electric signal, the noise and an out-band component are removed, thereby improving the S/N ratio of this signal. The pulse height signal generation circuit 34 further includes a peak hold circuit or a sample-and-hold circuit (both of which are not shown), and by holding the maximum value of the signal waveform after filtering, the signal of the voltage corresponding to the energy of the captured gamma ray is generated and outputted.

The timing signal generation circuit 35, when received with the amplified gamma ray detection signal, immediately outputs a timing signal which is a predetermined rectangular wave pulse. The time measurement circuit 32, based on the timing signal from the timing signal generation circuit 35, generates and outputs detection time data. To be more in detail, the time measurement circuit 32, based on the clock signal from a common clock signal generator (not shown) inside the nuclear medical diagnosis apparatus 100, generates detection time data for the received timing signal.

The pulse height measurement circuit 31 is a circuit for generating detection time data of the gamma ray detection signal for one gamma ray detection signal, pulse height data showing the energy of the detected gamma ray detection signal, and a data packet (detection data) outputting the gamma ray detection signal and including an identifier of the detector 24.

The pulse height measurement circuit 31 includes an A/D (analogue to digital) converter (not shown), and converts analog pulse height signal of the pulse height signal generation circuit 34 to digital signal, thereby generating the pulse height data. The pulse height measurement circuit 31 adds this pulse height data to the detection data generated by the time measurement circuit 32 and each information on the identifier of the detector 24 outputting the gamma ray output signal, thereby generating the data packet and outputting it to the data merge circuit 30.

The data merge circuit 30 includes an I/O merge function for integrating a plurality of input systems into one output system, and a buffer memory function for temporarily storing the received data packet and outputting it according to the processing speed of the configurational elements of the subsequent stage. The data merge circuit 30, when received with the data packet from each pulse height measurement circuit 31, performs the buffering thereof according to needs, and outputs the packet to the data merge IC 20. The data merge circuit 30 of each data acquisition IC 21 further includes a sort function for rearranging a plurality of buffered data packets, and outputting them in order of the detection time data. By performing the sort processing (processing for rearranging the plurality of data packets in order of the detection time data, that is, the processing for rearranging them in order of the detection time) in a dispersed manner by these data merge circuits 30, the concentration of a load into one data merge circuit can be avoided, and a circuit unit of the data merge circuit 30 can be reduced to a small-scale. Hence, the mounting of the data merge circuit 30 can be performed easily. Since this sort processing is performed every data packet integrated into a predetermined time frame, the processing load is further reduced.

The data merge IC 20 has a buffer function for receiving once the data packets from a plurality of data acquisition ICs 21 and a sort function for rearranging the buffered data packets in order of the detection time data. These data packets are outputted to the auxiliary data acquisition unit 2 from the detector unit 1 in order of the detection time data. The data merge IC 20 has a plurality of buffer memory elements (not shown), and during a predetermined time frame (for example, 16 "μs"), stores the received data packets in one buffer memory element, and at the same time, processes the data stored in the other buffer memory elements. The data merge IC 20, during the next time frame, processes the data packets stored in one buffer memory element, and at the same time, erases all the contents of the other buffer memory elements at the starting time of this time frame, and after that, stores the received data packets. By repeating such procedure, a load required for the rearrangement is reduced, and a control thereof can be simplified. When the speed of the processing speed and the miniaturization of the circuit scale are sought after, the processing is configured to be performed by using the higher-order bit of the detection time data. The data merge IC 20 includes a FIFO (first-in first-out) buffer, and processes the received data packets in sequence, so that the merging and rearrangement of the data packets may be performed.

The sort function of the data merge IC 20 may be replaced as follows. That is, the data merge IC 20 may be configured to take out in order the earliest data packets of the detection time data from among the head data packets held by a plurality of data acquisition ICs 21 and arrange them in order of the detection time data, and collect the predetermined number of data packets arranged in order of the detection time data and output them to the auxiliary data acquisition unit 2.

Although the data merge IC 20, the auxiliary data acquisition unit 2, and the data acquisition unit 3 are different in the processing ability and the circuit-scale, in these configurational elements, a mechanism (hereinafter, referred to as detection time sequence output mechanism) for arranging and outputting the plurality of data packets in order of the detection time data basically follows the same principle. Hence, the data merge IC 20, the auxiliary data acquisition unit 2, and the data acquisition unit 3 can take a circuit configuration based on the same fundamental concept. A specific example of the detection time sequence output mechanism in these configurational elements will be exemplarily described later when the configuration inside the data acquisition unit 3 is described in detail.

Referring back to FIG. 1, since the present embodiment is provided with four auxiliary data acquisition units 2, each data merge IC 20 of the detector units 1 of one fourth from among all the detector units 1 provided for the imaging apparatus 10 is connected to one auxiliary data acquisition unit 2. The auxiliary data acquisition unit 2 arranges the data packets from a plurality of detector units 1 in order of the detection time data, and outputs them to the data acquisition unit 3. The outputs of all the detector units 1 are configured to be not directly received at the data acquisition unit 3, but allow the plurality of auxiliary data acquisition units 2 to be interposed in-between, and by collecting the plurality of data packets in order of the detection time data by going through a plurality of stages, a data transmission path is decenterized so as to avoid the concentration of the wirings, and at the same time, the flexibility of the design of the data processing system can be improved. Since the data packets from the plurality detector units 1 are subjected once to the decenterized processing by the plurality of auxiliary data acquisition units 2, the processing loads of the auxiliary data acquisition units 2 and the data acquisition unit 3 are relatively reduced, and the circuit scales of both units need only be small, and the circuit can be mounted quite easily.

In the data acquisition unit 3 (see FIG. 3), the data sort section 50 outputs the plurality of data packets received from the plurality of auxiliary data acquisition units 2 in order of the detection time data. The coincidence detection section 51 judges the data packets relating to a pair of the gamma ray generated by the same event (that is, the data packet relating to the coincidence counting) from the data packets arranged in order of this detection time data. Specifically, the pair check section 52 sorts the plurality of data packets outputted from the data sort section 50 into those related to the coincidence counting and those not related. The pair generation section 53 combines a pair of the data packets related to the coincidence counting.

The function of the data sort section 50 will be specifically described below by using FIG. 4. The unit data buffer 65 is a buffer memory having a function for storing the data packets in an input order, a function for outputting the stored data packets in an input order, and a function for collectively erasing the stored data packets.

The change over switch 60 repeats the following change over operations (a1) and (a2) every time frame, and changes over the buffers connected to the auxiliary data acquisition unit 2.

(a1) The change over switch 60, in some time frame, connects the auxiliary data acquisition unit 2 and the first buffer 65*a*. At this time, the auxiliary data acquisition unit 2 is not connected to the second buffer 65*b*.

(a2) The change over switch 60, in the next time frame, connects the auxiliary data acquisition unit 2 and the second buffer 65*b*. At this time, the auxiliary data acquisition unit 2 is not connected to the first buffer 65*a*.

The change over switch 61 repeats the following operations (b1) and (b2) every time frame, and changes over the buffers connected to the unit sort circuit 66.

(b1) In some time frame, during the period when the change over switch 60 connects the auxiliary data acquisition unit 2 and the first buffer 65*a*, the change over switch 61 connects the second buffer 65*b* and the unit sort circuit 66. At this time, the first buffer 65*a* and the unit sort circuit 66 are not connected.

(b2) In the next time frame, during the period when the change over switch 60 connects the auxiliary data acquisition unit 2 and the second buffer 65*b*, the change over switch 61 connects the first buffer 65*a* and the unit sort circuit 66. At this time, the second buffer 65*b* and the unit sort circuit 66 are not connected.

Consequently, during the period when the first buffer 65*a* stores the data packet from the auxiliary data acquisition unit 2, the second buffer 65*b* outputs the stored data packet to the unit sort circuit 66. Contrary to this, during the period when the second buffer 65*b* stores the data packet from the auxiliary data acquisition unit 2, the first buffer 65*a* outputs the stored data packet to the unit sort circuit 66. In this manner, the change over is performed, and thus, even when the data processing is performed every time frame, the plurality of data packets are continuously processed.

The first buffer 65*a* (or the second buffer 65*b*) that has finished outputting the stored data packets starts storing new data packets at a point of time when the time frame is changed to the next time frame, and therefore, collectively erases the data packets already stored. The first buffer 65*a* and the second buffer 65*b* preferably have a sufficient capacity to store the data packets expected to be outputted during one time frame from the auxiliary data acquisition unit 2. However, when the first buffer 65a (or the second buffer 65b) is inputted with the data packets exceeding the capacity during one time frame, the data packets that exceed the capacity are destroyed. When the first buffer 65a and the second buffer 65b have practically sufficient capacity in this manner, the reduction of the circuit scale can be attained.

The unit sort circuit 66, when reading the stored data packets from the first buffer 65a (or the second buffer 65b), has a function for allowing the data packets from a plurality of first buffers 65a (or a plurality of second buffers 65b) to be outputted in order of the detection time data. Specifically, the unit sort circuit 66 retrieves and reads the data packet including the earliest detector time data from among each data packet of the respective four first buffers 65a (or four second buffers 65b) which is not yet read and positioned at the most output terminal side. The unit sort circuit 66 adds the read data packet to the rearmost end of the data packet column expected to output the read data packet. This data packet column includes the plurality of data packets arranged in order of the detection time data. The unit sort circuit 66, as described above, repeats taking out the data packet including the earliest detection time data and adding the same to the rearmost data packet column. In the first buffer 65a (or the second buffer 65b), the taken out data packet is set a flag showing that it is taken out.

The first buffer 65a and the second buffer 65b, when the data packet positioned at the most output end side is read, may be configured to erase this data packet, and shift the stored residual data packets to the output side one by one. Alternatively, the already or not yet read data address is kept held, so that the head data packet not yet read may be allowed to be recognized.

The unit sort circuit 66, as described above, collects a predetermined number of data packets read in order of the detection time data (in order of the detection time) in this order, and outputs them to the change over switch 62. Since the unit sort circuit 66 collects and outputs the plurality of data packets arranged in advance in the detection time order in this manner, when comparing with the case where a large number of data packets are collected and sorted, the processing load need only be small, and the downsizing of a circuit scale or the speeding up of the processing speed can be attained.

The delayed data buffer 67 is a buffer memory having a function for storing the data packets in the input order, a function for outputting the stored data packets in the input order, and a function for collectively erasing the stored data packets. Each buffer (67a to 67c) of the delayed data buffer 67, even when performing the output of the data packets until performing the collective erase operation to be described later, holds the memory content. Consequently, each buffer (67a to 67c) has the same memory content read twice, respectively.

The change over switch 62 repeats the following operations (c1) to (c3) every time frame, and changes over the buffers connected to the unit sort circuit 66.

(c1) The change over switch 62, in some time frame, connects the unit sort circuit 66 and the first buffer 67a. At this time, the unit sort circuit 66 is not connected to the second buffer 67b and the third buffer 67c.

(c2) The change over switch 62, in the next time frame, connects the unit sort circuit 66 and the second buffer 67b. At this time, the unit sort circuit 66 is not connected to the first buffer 67a and the third buffer 67c.

(c3) The change over switch 62, further in the next time frame, connects the unit sort circuit 66 and the third buffer 67c. At this time, the unit sort circuit 66 is not connected to the first buffer 67a and the second buffer 67b.

The change over switch 63 repeats the following operations (d1) to (d3) every time frame, and changes over the buffers connected to the delayed data sort circuit 68.

(d1) In some time frame, during the period when the change over switch 62 connects the unit sort circuit 66 and the first buffer 67a, the change over switch 63 connects the second buffer 67b and the third buffer 67c with the delayed data sort circuit 68. At this time, the delayed data sort circuit 68 is not connected to the first buffer 67a.

(d2) In the next time frame, during the period when the change over switch 62 connects the unit sort circuit 66 and the second buffer 67b, the change over switch 63 connects the first buffer 67a and the third buffer 67c with the delayed data sort circuit 68. At this time, the delayed data sort circuit 68 is not connected to the second buffer 67b.

(d3) Further in the next time frame, during the period when the change over switch 62 connects the unit sort circuit 66 and the third buffer 67c, the change over switch 63 connects the first buffer 67a and the second buffer 67b with the delayed data sort circuit 68. At this time, the delayed data sort circuit 68 is not connected to the third buffer 67c.

Consequently, during the period when the first buffer 67a stores the data packets from the auxiliary data acquisition unit 2, the second buffer 67b and the third buffer 67c output the stored data packets to the unit sort circuit 66. Likewise, in another time frame, the connecting destinations of the input terminal and the output terminal of each of the buffers (67a to 67c) are changed over, and the same operation is performed.

Since the buffer (any of 67a to 67c) having outputted the stored data packets starts storing new data packets at a point of time when the time frame relating to the double output of the data packets is completed, the stored data packets are collectively erased. Although all the buffers (67a to 67c) preferably have sufficient capacities to store the data packets outputted from all the auxiliary data acquisition units 2 during one time frame, when the data packets remaining unstorable are inputted, similarly to the buffers 65a and 65b, they are destroyed.

The delayed data sort circuit 68 has a function for collectively outputting a predetermined number of each data packet stored in the delayed data buffer 67 in order of the detection time data. The order of the detection time data in this case means a relative time order to circulate by taking the starting time of the time frame as the smallest value and the completion time of this time frame as the maximum value. In other words, since every start of a new time frame, the referent time of this relative time is initialized, when the data packets relative to a plurality of time frames are arranged in order of this relative time, the data packets relating to the different time frame are mixed, and are lined up in tandem.

The delayed data sort circuit 68 retrieves and reads the data packets including the earliest detection time data from among each data packet not yet read and positioned at the most output end side of each of the two buffers connected by the change over switch 63 from among the buffers 67a, 67b, and 67c. The delayed data sort circuit 68 adds the read data packets to the rearmost end of the data packet column scheduled to output. The delayed data sort circuit 68, as described above, repeats reading the data packets including the earliest detection time data and adding them to the rear most end of the data packet column. In the buffer 67a, 67b, and 67c, the read data packets are set with a flag showing that they are read.

When each data packet from the above described two buffers is read, the delayed data sort circuit 68 erects a flag 'p' (prompt) to each data packet (new data packet) read from the buffer storing the data packets subsequently from among the two buffers (two from any of 67a to 67c). The delayed data sort circuit 68 erects a (delayed) flag 'd' to each data packet (old data packet) read from the buffer storing the data packets first from among those two buffers. When the absolute time is taken as a reference, the old data packet set with the flag 'd' is a data packet in one time frame ahead of the new data packet set with the flag 'p'.

That is, each buffer of the delayed data buffer 67 repeats the following procedures (e1) to (e3) by changing over the change over switches 62 and 63 every time frame.

(e1) The first buffer 67a: stores the data packet from the unit sort circuit 66.

The second buffer 67b: outputs the data packet to the delayed data sort circuit 68. This data packet is set with a flag 'd' by the delayed data sort circuit 68.

The third buffer 67c: outputs the data packet to the delayed data sort circuit 68. This data packet is set with a flag 'p' by the delayed data sort circuit 68.

(e2) The first buffer 67a: outputs the data packet to the delayed data sort circuit 68. This data packet is set with a flag 'p' by the delayed data sort circuit 68.

The second buffer 67b: stores the data packet from the unit sort circuit 66. The third buffer 67c: outputs the data packet to the delayed data sort circuit 68. This data packet is set with a flag 'd' by the delayed data sort circuit 68.

(e3) The first buffer 67a: outputs the data packet to the delayed data sort circuit 68. This data packet is set with a flag 'd' by the delayed data sort circuit 68.

The second buffer 67b: outputs the data packet to the delayed data sort circuit 68. This data packet is set with a flag 'p' by the delayed data sort circuit 68.

The third buffer 67c: stores the data packet from the unit sort circuit 66.

The buffers (67a to 67c) hold a pointer of the head data address not yet read, and when one head data packet is read, this pointer is shifted to the next address of the data packet. Consequently, referring to this pointer, the head data packet not yet read is read. Since the buffers (67a to 67c) have the stored data of the same content read twice, the position of the pointer showing the head data address is restored at the starting time of the time frame, but during that time, the stored data packets are not erased. When a starting time of the time frame for storing new data packets comes, all the stored data packets are erased.

The delayed data sort circuit 68 outputs a plurality of data packets thus processed and collected into a predetermined number in order of the detection time data to the coincidence detection section 51. Since the delayed data sort circuit 68 collects and outputs the predetermined number of data packets thus arranged in advance in order of the detection time, the processing load need only be small, and the circuit scale can be made small and the processing speed can be speeded up.

As shown in FIG. 5, the pair check section 52 has a function for comparing in order the data packets transmitted from the data sort section 50, and checking whether or not a pair of the coincidence countings is present in the data, and erecting a coincidence counting flag for the pair of coincidence countings, and erecting a delayed coincidence counting flag for the pair of delayed coincidence countings.

Each data packet inputted to the pair check section 52 of the coincidence detection section 51 includes the delayed flag assuming the value of 'p' or 'd' in addition to the identifier, the detection time data, and the pulse height data of the detector 24. The pair check section 52, when inputted with the data packet, outputs the data packet further added with a flag area for writing each flag to be described later to a pair generation section 53.

The flags set in the flag area in the pair check section 52 are a coincidence counting flag, a coincident counting position flag, a delayed coincidence counting flag, and a delayed coincidence counting position flag. The coincidence counting flag and the delayed coincidence counting flag assume three values of 'none', 'valid', and 'data invalid'. The coincidence counting position flag and the delayed coincidence counting position flag, when a pair is present in the data packets following their own data packets, assume the distance (for example, the number of stages of the register) up to the data packets that make a pair as a value, and in the case otherwise, assume a value '0'. The initial value of these flags is '0'.

A comparison data register 70 of the pair check section 52 receives in order the data packets outputted from the delayed data sort circuit 68 to a register 70a positioned at an input terminal in the detection time data order, and allows each data packet to shift on the registers at every stage on the way by one clock each toward the register 70e positioned at the output terminal. The comparison data register 70 stores a total of five data packets in the registers 70a to 70e with one each for every register.

Each of the comparators 75a to 75d performs a comparison of the data packet stored in the register 70e with the data packet stored in one relevant register from among the registers 70a to 70d. The comparators 75a to 75d judges whether or not the difference (referred to as detection time difference) of the detection time data of the two data packets serving as a comparison object enterers within a predetermined coincidence detection allowable time (time window) (judgment of the detection time difference), and based on the identifiers of the detectors 24 of these two data packets, judges whether or not the positions of these detectors 24 are in the probable range as synchronous events (judgment of the detection positions).

The coincidence detection circuit 76 has a function for finding out a pair of the data packets servable as the coincidence counting or the delayed coincidence counting based on each output of the comparators 75a to 75d. The first judging section 74a receives two pieces of judgment information (judgment information on the time window and judgment information on the detector position) from the comparator 75a, and when the detection time difference enters the time window and the two detector positions are in the probable range as the simultaneous event, and when the delay flags of two data packets inputted to the comparator 75a are concurrently 'p', the coincidence counting is judged. When the first judging section 74a has two pieces of the judgment information satisfied as described above, and the delay flags of those data packets are the combination of 'p' and 'd' or 'd' and 'p', the delayed coincidence counting is judged. When the delay flags of the two data packets are concurrently 'd', the judgment of the coincidence counting and the delayed coincidence counting is not performed. Other first judging sections 74b to 74d also perform the same judgment processing as the first judging section 74a based on the two pieces of the judgment information inputted from the comparators 75b to 75d.

The second judging section 73 of the coincidence detection circuit 76, when the first judging sections 74a to 74d judge one coincidence counting, judges it as a pair of effective data packets, and turns the coincidence counting flag of this pair of the data packets into 'valid', and writes the distance (the number of stages) up to the register (any one of 70a to 70d) on which the data packet used as a pair is positioned in a coincidence counting position flag of the data packets inside the register 70e serving as a reference.

When two or more sets of the pair of the data packets for which the coincidence counting judgment was performed are available, it is not possible to judge which pair of the data packets is right. Hence, the second judging section 73 changes all the 'valid' of the coincidence counting flags of these data packets inside the register 70e to the 'data invalid'. When a pair of the coincidence countings is available in the five data packets stored inside the comparison data register 70, that pair should surely make a pair.

In the present embodiment, the processing is performed by mixing two pairs of the data packets mutually shifted by one time frame.

When two or more pairs of the data packets subjected to the delayed coincidence counting judgment are available, it is not possible to judge which pair of the data packets is right. Hence, the second judging section 73 changes all the 'valid' of the delayed coincidence counting flags of these data packets inside the register 70e to the 'data invalid'. Similarly to the coincidence counting, when a pair of the delayed coincidence countings is available from among the five data packets stored inside the comparison data register 70, that pair should surely make a pair.

The comparison of the data packets, the adding up of the coincidence counting or the delayed coincidence counting, the flag erection of the data packets stored in each register, and the like may be configured to be performed by a pipe line processing. These processings are performed with the same clock taken as a reference, so that the circuit can be simplified, and at the same time, the throughput can be improved. In this case, between the pair check section 52 and the pair generation section 53, a data register (not shown) for a delay portion by the pipe line processing is inserted.

The pair generation section 53 has a function for selecting a pair of data packets relating to the coincidence counting or the delayed coincidence counting by referring to the coincidence counting flag and the delayed coincidence counting, integrating these two pieces of the data packet, generating a data packet relating to the coincidence counting or the delayed coincidence counting, and outputting it to the collection work station 5 of an acquisition console 4. The pair data register 72 is a shift register that connects the registers 72a to 72e in series in the forward direction, and shifts the data packet stored every one time frame a stage by a stage, and receives and outputs the data packet at input and output terminals.

The pair data generation circuit 78 confirms the data packet of the register 72e, and when the coincidence counting flag or the delayed coincidence counting flag of this data packet is 'valid', controls the selectors 77a to 77d of the data selector 77, and takes out the data packets used as a pair. When both of the data are effective, the two pieces of the data packet are integrated and outputted as one data packet. Since the data packet includes those relating to the ordinary coincidence counting and those relating to the delayed coincidence counting, the data used as a pair is taken out separately, respectively.

Figure 7:
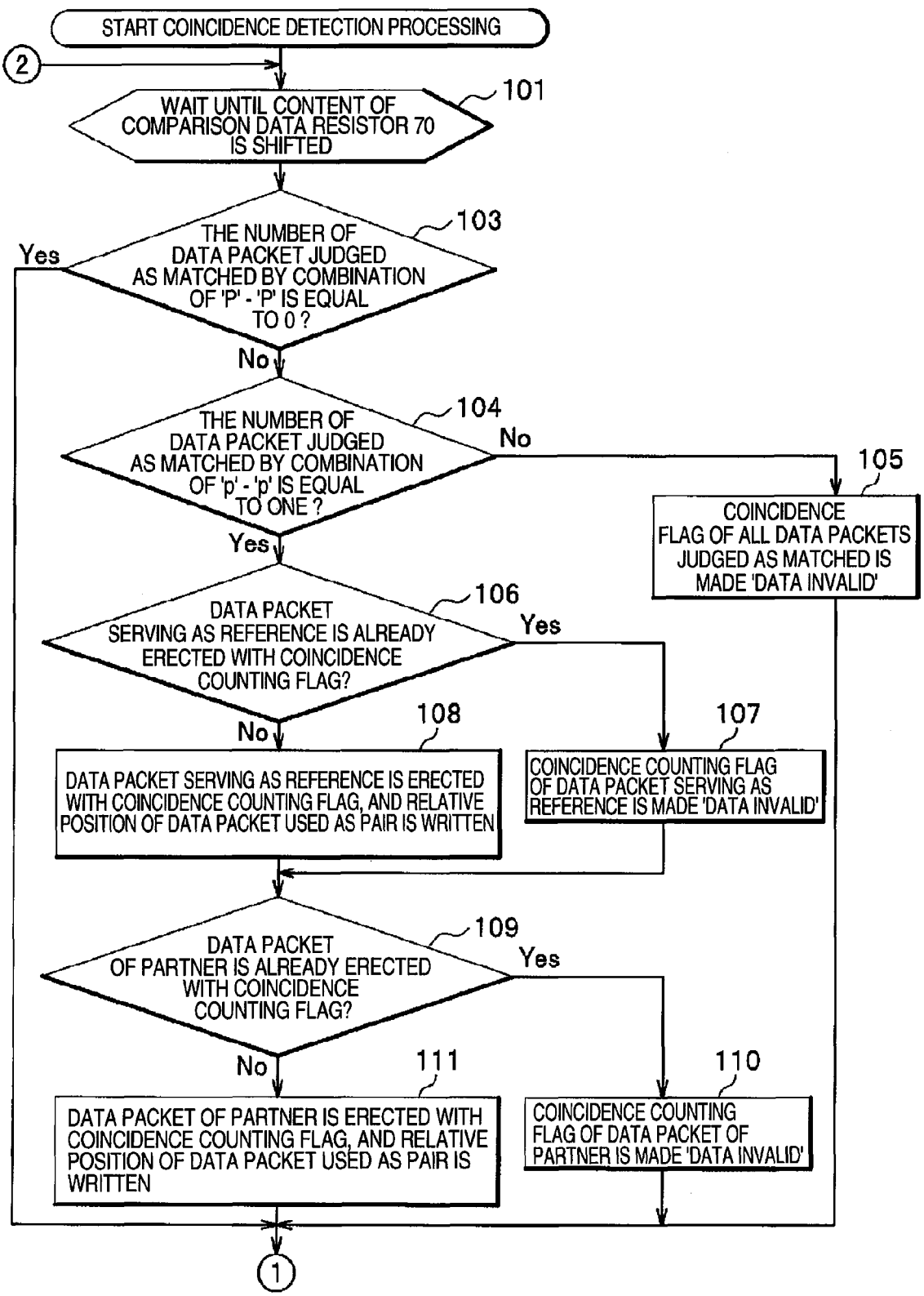
FIG. 7 is a flowchart (first surface) showing a coincidence detection processing.
Figure 8:
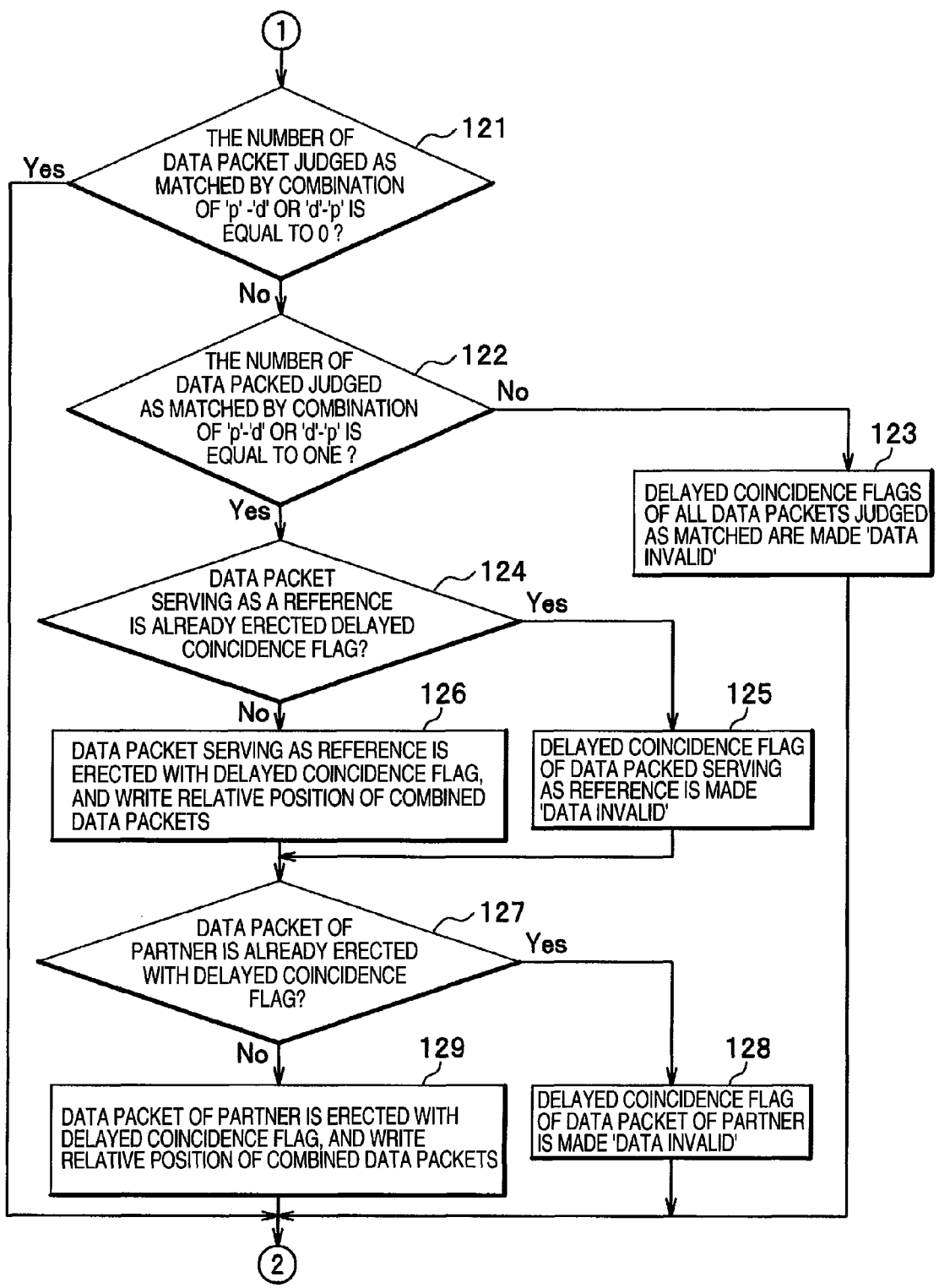
FIG. 8 is a flowchart (second surface) showing a coincidence detection processing.

Referring to FIGS. 7 and 8, the coincidence detection circuit 76, specifically, the coincidence counting judgment processing performed in the second judging section 73 will be described.

First, the second judging section 73 waits until a new data packet is shifted to the register 70e in the comparison data register 70 (step 101).

The second judging section 73, after the new data packet is stored in the register 70e, executes the processings of steps 103 to 111 (processings relating to the coincidence counting) shown in FIG. 7 and steps 121 to 129 (processings relating to the delayed coincidence counting) shown in FIG. 8. When the new data packet is stored in the register 70e, the second judging section 73, first, based on the output information from the comparators 75a to 75d, executes the following processings relating to the coincidence counting. That is, it is judged whether or not the data packets in which the delayed flag is a combination of 'p' and 'p' and which is judged as matched are equal to 0 (step 103). When "Yes", the processing of step 121 described later is executed. When the judgment is "No", the second judging section 73, by using those pieces of the output information, judges whether or not the data packets in which the delayed flag is a combination of 'p' and 'p' and which is judged as matched are equal to one (step 104). When this judgment is "No", the coincidence counting flags of all the data packets judged as matched are changed to 'data invalid' (step 105) and the processing proceeds to step 121. When the judgment of step 104 is "Yes", it is judged whether or not the coincidence counting flag is already set in the data packet serving as a reference stored in the register 70e (step 106). When the judgment of step 106 is "Yes", the coincidence counting flag of this data packet serving as the reference is changed to 'data invalid' (step 107), and the processing proceeds to step 109. When the judgment of step 106 is "No", the coincidence counting flag is set in the data packet serving as the reference, and at the same time, a relative position with the data packet used as a pair is written (step 108). Next, it is judged whether or not the coincidence counting flag is already set in the data packet of the partner of the pair (step 109). When this judgment is "Yes", the coincidence counting flag of the packet of the partner of the pair is changed to 'data invalid' (step 110), and the processing proceeds to step 121. When the judgment of step 109 is "No", the coincidence counting flag is set in the data packet of the partner of the pair, and at the same time, a relative position ('0' due to an opposite position) with the data packet used as a pair is written (step 111).

After the processing relating to the coincidence counting thus described above is completed, the second judging section 73, based on the output information from the comparators 75a to 75d, executes the processing relating to the delayed coincidence counting as shown in FIG. 8. That is, it is judged whether or not the data packets in which the delayed flag is a combination of 'p' and 'd' or 'd' and 'p' and which is judged as matched are equal to zero (step 121). When this judgment is "Yes", the coincidence counting judgment processing is completed, and the processing returns to step 101 and waits until the next data packet (data packet stored in the register 70d) serving as the reference is shifted to the register 70e. After the new data packet serving as the reference is shifted to the register 70e, the processings of steps 103 to 111 and steps 121 to 129 are repeated.

When the judgment of step 121 is "Yes", it is judged whether or not the data packets in which the delayed flag is a combination of 'p' and 'd' or 'd' and 'p' and which is judged as matched are equal to one (step 122). When this judgment is "Yes", the delayed coincidence counting flags of all the data packets judged as matched are changed to 'data invalid' (step 123), and as described above, the processing returns to step 101, and the predetermined processing is repeated. When the judgment of step 122 is "Yes", it is judged whether or not the delayed coincidence counting flag is already set in the data packet serving as the reference stored in the register 70e (step 124). When the judgment of step 124 is "Yes", the delayed coincidence counting flag of this data packet serving as the reference is changed to 'data invalid' (step 125), and after that, the processing of step 127 is executed. When the judgment of step 124 is {No}, the delayed coincident counting flag is set in the data packet serving as the reference, and a relative position with the data packet used as a pair of combination is written (step 126). Next, it is judged whether or not the delayed coincidence counting flag is already set in the data packet of the partner of the pair (step 127). When this judgment is "Yes", the delayed coincidence counting flag of the data packet of the partner of the pair is changed to 'data invalid' (step 128), and as described above, the processing returns to step 101, and the predetermined processing is repeated. When the judgment of step 127 is "No", the coincidence counting flag is set in the data packet of the partner of the pair, and a relative position ('0' due to an opposite position) with the data packet used as a pair is written (step 129). After that, the processing returns to step 101, and the predetermined processing is repeated.

Figure 9:
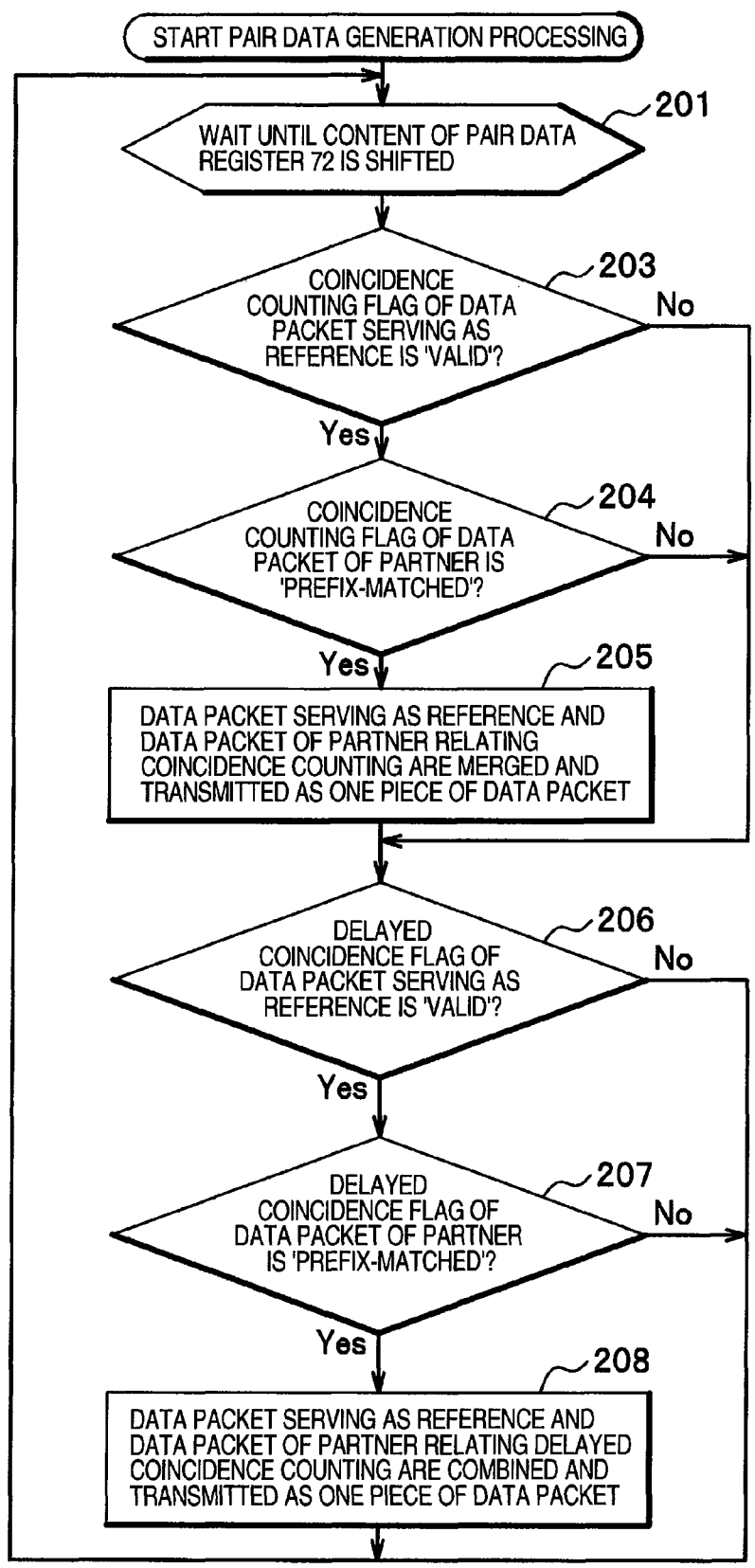
FIG. 9 is a flowchart showing a pair data generation processing in a coincidence counting processing.

Referring to FIG. 9, a pair data generating processing executed in the pair generation section 53 inside the coincidence detection section 51, specifically, in the pair data generation circuit 78 will be described.

First, the pair data generation circuit 78 waits until a new data packet is shifted to the register 72e in the pair data register 72 (step 201).

The pair data generation circuit 78, after the new data packet is stored in the register 72e, executes the processings of steps 203 to 205 (processing relating to the coincidence counting) and the steps 206 to 208 (processing relating to the delayed coincidence counting) shown in FIG. 9. When the new data packet is stored in the register 70e, the pair data generation circuit 78, first, based on the output information from the selectors 77a to 77d, executes the following processings relating to the coincidence counting. That is, it is judged whether or not the coincidence counting flag of the data packet serving as the reference is 'valid' (step 203). When this judgment is "No", the processing of step 206 is executed. When the judgment is "Yes", it is judged whether or not the coincidence counting flag of the data packet of the partner of the pair is 'forward-matched' (step 204). When this judgment is "No", the processing of step 206 is executed. When this judgment is "Yes", the data packet serving as the reference and the data packet of the partner relating to the coincidence counting are integrated into one data packet, and this is transmitted to the collection work station 5 (step 205).

Next, the pair data generation circuit 78, based on the output information from the selectors 77a to 77d, executes the processing relating to the delayed coincidence counting. That is, it is judged whether or not the delayed coincidence counting flag of the data packet serving as the reference is 'valid' (step 206). When the judgment of step 206 is "No", as described above, the processing returns to step 101, and the predetermined processing is repeated. When the judgment is "Yes", it is judged whether or not the delayed coincidence counting flag of the data packet of the partner of the pair is 'forward-matched' (step 207). When this judgment is "No", the processing returns to step 201, and the predetermined processing is repeated. When the judgment is "Yes", the data packet serving as the reference and the data packet of the partner relating to the delayed coincidence counting are integrated into one data packet, and this is transmitted to the collection work station 5 (step 208). The processing returns to step 201 and the predetermined processing is repeated.

The coincidence counting detection processing (see FIGS. 7 and 8) and the pair data generation processing (see FIG. 9) are executed in parallel during one clock on the plurality of data packets.

Figure 10A:
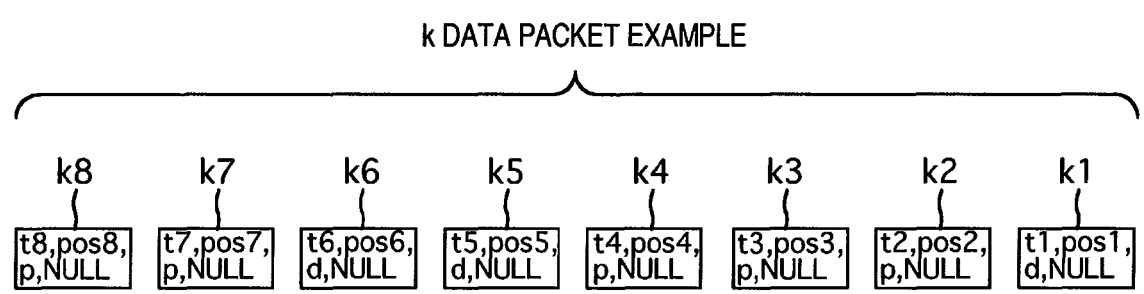
FIG. 10A is a diagram showing a processing example of a data packet in a coincidence detection section.
Figure 10B:
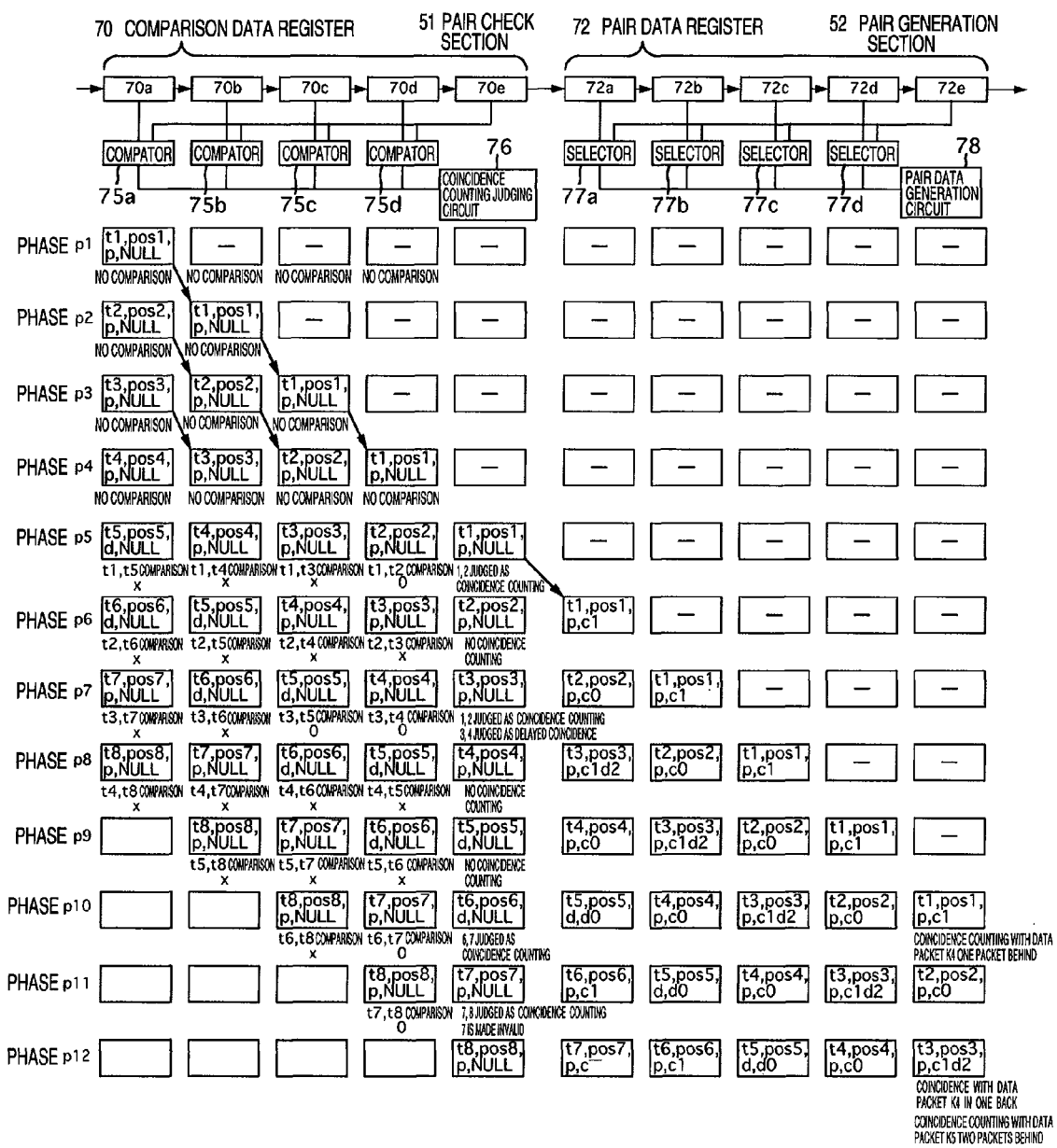
FIG. 10B is a diagram showing a processing example of a data packet in a coincidence detection section.

Referring to FIGS. 10A and 10B, an example will be described in which the data packet is subjected to the coincidence detection and the delay coincidence detection. The data packet columns shown in FIG. 10A, as shown in FIG. 10B, when inputted to the coincidence detection section 51 in order, are processed by the processing procedures and the like in the pair check section 52 and the pair generation section 53 as shown in FIGS. 7 to 9, and are outputted in order from the coincidence detection section 51 to the collection work station 5.

First, in the initial state (not shown), the data packet is stored in neither the registers 70a to 70e nor 72a to 72e. The time interval of each phase is the same as the time width of one clock. Consequently, as every one clock portion time elapses, the phase number advances by one number each ahead. As the phase number advances by one number each ahead, each data packet stored in the registers 70a to 70e and 72a to 72e is shifted to the next register one by one in the forward direction.

In a phase p1, a data packet k1 is inputted to the pair check section 52, and is stored in the register 70a. Each information included in the data packet will be described with the data packet k1 taken as an example. Those pieces of the information include a flag area containing a detection time data (t1), an identifier (pos1) of the detector 24, a delay flag ('p' or 'd') showing whether or not it is a data delayed by one time frame, and flag information obtained by the coincidence counting processing. All the initial values of the flag area are "0" (NULL).

In the phase p1, the register 70e is not stored with the data packet. Hence, in the phase p1, the coincidence between is not performed. In phases p2 to p4, since the new data packets k2 to k4 are inputted in order, the data packets are stored in order in the registers 70a to 70d by inputting or shifting. However, since the head register 70e is not stored with the data packet, the coincidence between is not performed.

In a phase p5, the data packet k1 is stored in the register 70e of the last stage. The comparators 75a to 75d compare and process the data packet k1 serving as the reference stored in the register 70e and each of the data packets k2 to k5 stored in the resistors 70a to 70d, respectively. Specifically, each of the comparators 75a to 75d, by using one relevant data packet from among the data packet k1 and the data packets k2 to k5, as described above, judges whether or not the detection time difference enters the time window and whether or not two detection positions are probable positions as the coincidence counting or the delayed coincidence counting. The coincidence detection circuit 76, based on the judging information from the comparators 75a to 75d, judges a pair of the data packets satisfying these two requirements as the coincidence counting or the delayed coincidence counting (the first judging sections 74a to 74d). In this example, though the data packets k1 and k2 satisfy the requirement as the coincidence counting, other combinations shall not be taken as satisfying the requirement as the coincidence counting. In this case, the coincidence detection circuit 76 judges that, since the delay flags of such data packets k1 and k2 are concurrently 'p', they are a pair of the coincidence counting.

The coincidence detection circuit 76, when the coincidence counting judgment is performed, turns the coincidence counting flag, which shows that a pair of the coincidence countings are present in the data packet serving as the reference, into 'valid' (specifically 'c' (coincidence)), and writes a value (the number of stages of the register) showing how much the data packet used as a pair is delayed from the data packet serving as the reference into the coincidence counting position flag (the second judging section 73). In this example, 'c' and 'c1' showing a relative position '1' of the data packet k2 for the data packet k1 are set as a coincidence counting flag and a coincidence counting position flag (hereinafter, represented by coincidence counting (position) flag, which means both flags) in the flag area of the data packet k1. In the flag area of the data packet k2 used as a pair, 'c' showing the presence of the pair of the coincidence counting and 'c0' meaning the positional information '0' showing a previous presence prior to itself of the data packet preparing a pair are set as the coincidence counting (position) flag. When the judgment of the detection time difference and the judgment of the detection position are concurrently "No" or the delay flags of the two data packets performing the coincidence between are concurrently 'd', the value of the flag area of the relevant data packet is still the initial value.

In a phase p6, the data packet k1 is stored in the register 72e, and the data packet k2 is stored in the register 70e. Hence, the coincidence between is performed with the data packet k2 as a reference. For each of the data packet k2 and the subsequent data packets k3 to k6, each judgment of the detection time difference and the detection position becomes "No". Hence, the coincidence detection circuit 76 does not change the value of the flag area. In the phase 6, the data packet k1 set with the coincidence counting (position) flag is stored in the register 72a of the pair generation section 53. However, since the register 72e is not stored with the data packet, the pair data generation circuit 78 does not perform the pair data generation processing.

In a phase p7, a data packet k3 is stored in the register 70e. In the phase p7, the data packet k3 and each of data packets k4 and k5 are compared, respectively. As a result, both of the data packets k3 and k4 have the delay flags of 'p', and therefore, they are judged as the coincidence counting data. The data packets k3 and k5 have the delay flag of 'p' for the former and the delay flag of 'd' for the latter, and therefore, they are judged as the delayed coincidence counting. Hence, in the data packet k3, a value 'c1' showing that it is the coincidence counting and makes a pair with the data packet k4 one packet behind is set as the coincidence counting (position) flag, and at the same time, a value 'd2' showing that it is the delayed coincidence counting and makes a pair with the data packet k5 two packets behind are set as the delayed coincidence counting (position) flag. The data packet k4 is set with 'c0' as the coincidence counting (position) flag, and the data packet k5 is set with 'd0' as the delayed coincidence counting (position) flag.

In phases p8 and p9, since a pair applicable to the coincidence counting or the delayed coincidence counting cannot be found out, the data packets k1 to k8 are shifted in the forward direction. In a phase p10, since the data packets k6 and k7 are matched, the data packet k6 is set with 'c1' as the coincidence counting (position) flag, and the data packet k7 is set with 'c0' as the coincidence counting (position) flag.

In a phase p11, since the data packets k7 and k8 are matched, though the data packets k7 and k8 are set with the coincidence counting (position) flag, with respect to the data packet k7, the coincidence counting flag is already set. That the flag is already set means that the pairs relating to the matching of not less than two pairs are present. When the data packet k7 already set with the flag is to be further set with the flag, the pair of the coincidence countings cannot be decided. Hence, 'c-' showing that the 'data is invalid' is set as the coincidence counting (position) flag. This holds true with the case where the matching of two or more pairs are judged at the same time by the comparator 75a to 75d.

In a phase p10, since the register 72e is stored with the data packet k1, the pair data generation circuit 78 performs the pair data generation processing. The pair data generation circuit 78 refers to the coincidence counting flag (or the delayed coincidence counting flag) of the data packet k1 stored in the register 72e, and judges a presence or absence of the data packet used as a pair. Since the value of the coincidence counting (position) flag of the data packet k1 is 'c1', it is known that the data packet used as a pair of the coincidence between is present one stage behind. Hence, referring to the coincidence counting (position) flag of the data packet k2, it is confirmed that this data packet k2 is valid, and the data packets k1 and k2 are taken out, and they become one piece of data packet of the coincidence counting, and this is transmitted to the collection work station 5. Presumably under the condition that the data packet k2 can further make a pair with any of the trailing data packets k3 to k8, the coincidence detection circuit 76 turns the coincidence counting (position) flag of the data packet k2 into 'data invalid'. As a result, a wrong coincidence between can be avoided.

In the phase 11p, though the data packet k2 is set with the coincidence counting (position) flag 'c' showing a coincidence counting, since the data packet used as a pair is present ahead, the pair data is not generated.

In a phase p12, for the data packet k3, the data packet k4 is judged as the coincidence counting, and the data packet k5 is judged as the delayed coincidence counting. Therefore, the pair data generation circuit 78 transmits the data packet of the coincidence counting that integrates the data packets k3 and k4 into one piece and the data packet of the delayed coincidence counting that integrates the data packets k3 and k5 into one piece to the collection work station 5, respectively.

In this manner, in the coincidence detection section 51, since the flag processing relating to the coincidence counting judgment and the delayed coincidence counting judgment can be independently performed in the same circuit, the circuit can be simplified. Further, the comparators 75a to 75e are shared by the coincidence counting processing and the delayed coincidence counting processing, and therefore, the circuit scale is reduced.

The data packet is given a flag for reference, and the comparison of the data packet is performed for only the data packet serving as a reference and the data packet following this data packet. Therefore, the processing load need only be small, and the circuit scale is reduced. The comparison processing can be performed regardless of whether or not the data packet is set with the flag, so that the comparators 75a to 75d are operated in collaboration and the pipeline processing of the data packet can be performed. As a result, the throughput of the pair check section 52 is increased, and the processing capability of the coincidence detection section 51 can be enhanced. The collection work station 5 performs the data processing based on the data packet of the coincidence counting which is inputted from the data acquisition unit 3, thereby generating PET data (tomogram information). A data storage (storage unit) 7 stores the generated tomogram information. A display device 6 displays the tomogram information read from the data storage. While a configuration has been illustrated in which the nuclear medical diagnosis apparatus 100 includes one set of the collection work station 5, depending on the content of the processing, the processing load, and the like, the collection work station 5 (not shown) may be further provided.

Erasure of the data packets stored in the first buffer 65a and the second buffer 65b may be carried out as follows. That is, the first buffer 65a and the second buffer 65b, when the head data packet positioned at the most output side is read, erases this data packet, and shifts the remaining stored data packets to the output end side one by one. Alternatively, the data address already read or not yet read is kept stored, and the head data packet not yet read may be made recognizable.

According to the nuclear medical diagnosis apparatus 100 of the present embodiment, the following advantages can be obtained.

The data coming out from one detector unit is taken as one event portion only in a time frame, and in the coincidence counting circuit for performing the coincidence between each detector unit, as the number of detector units increases, the number of coincidence detection circuits also increases in proportion to the square of the number of detector units. However, in the nuclear medical diagnosis apparatuses 100 and 100B of the present embodiment, since a plurality of events inside the time frame are processed every time frame, the number of coincidence between circuit need only be small, and the circuit scale can be reduced.

Different from the configuration in which the data from the detector unit is directly inputted to the coincidence counting circuit, in the present embodiment, while the data packets outputted from the detector units 1 and 1B during one time frame are stored in one buffer (for example, the first buffer 65a), the data stored in another buffer (for example, the second buffer 65b) is utilized so as to perform the processing of the subsequent stage. For this reason, the following advantages can be obtained.

(a) Since the storing and outputting of the data packet are shared alternatively by two buffers (65a and 65b), even when a large number of events occur in a time frame, the processing can be performed. Hence, the time frame can be set long, and a count loss of the detection data crossing over the time frame can be reduced.

(b) Since the data packets are arranged in advance on the basis of the detection time, the number of data packets serving as the target of the coincidence counting judgment is restricted, and the processing load becomes small, and the speeding up of the operation, and the reduction of the circuit scale can be attained.

(c) Since the present embodiment shares the judging circuit of the delayed coincidence counting with the judging circuit of the coincidence counting, the configuration in the PET apparatus, particularly, the circuit configuration can be simplified. The delayed time in the delayed coincidence counting is the same as the time of the time frame, and can cause a large time delay, so that mixing from the normal data in the delayed coincidence counting can be prevented. By further using the data increased in the delayed amount according to needs, the number of counts of the delayed coincidence counting can be increased.

(d) Since the delayed coincidence counting is performed, from among the coincidence-counted packet data (having a coincidence counting flag) inputted to the collection work station 5 serving as a tomogram creating apparatus, an inference of a wrong packet data can be easily performed. Specifically, by a ratio of the coincidence-counted packet data to the delayed coincidence-counted packet data (having a delayed coincidence counting flag), it is presumed that the coincidence-counted packet data is mixed with a wrong packet data. The packet data of that ratio is subtracted from the coincidence-counted packet data, and by using the remaining packet data, a tomogram is created, so that the obtained tomogram can be made sharp and clear. As a result, diagnosis accuracy for the small cancer can be improved.

Second Embodiment

Figure 11:
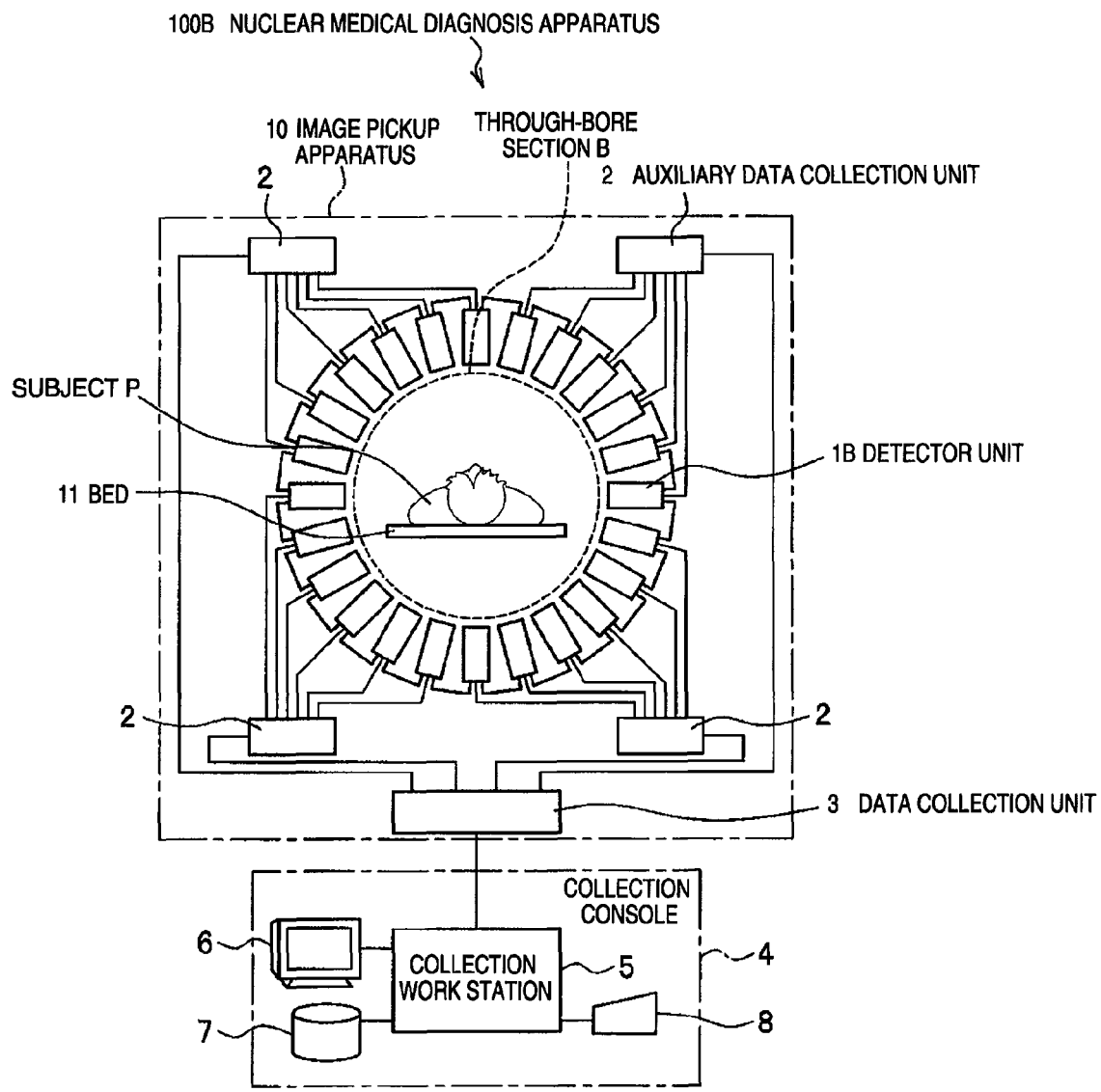
FIG. 11 is a block diagram showing a nuclear medical diagnosis apparatus according to a second embodiment of the present invention.

As shown in FIG. 11, a nuclear medical diagnosis apparatus 100B which is a second embodiment of the present invention is a PET apparatus, and has a configuration in which the detector unit 1 in the nuclear medical diagnosis apparatus of the first embodiment is replaced by a detector unit 1B. The nuclear medical diagnosis apparatus 100B has a configuration in which the mutually adjacent detector units 1B are connected so as to be transferable with the data for the purpose of detector scatter restoration process. Consequently, the configuration other than the above described configuration of the nuclear medical diagnosis apparatus 100B is the same as the nuclear medical diagnosis apparatus 100. The technique relating to the detector scatter restoration process in the present embodiment is also applicable to a SPECT (Single Photon Emission Computed Tomography) apparatus in addition to the PET apparatus.

Referring to FIGS. 11 and 2, the outline of the detector scatter restoration process will be described. A part of the radiation such as a gamma ray emitted from inside a subject P is captured and detected by a detector 24 inside the detector unit 1B arranged around the subject p. It is convenient for performing the detection to release all the energy of one gamma ray as an electric energy in one the detector 24 on which one gamma ray is incident in the first place.

However, in reality, a part of the energy of one gamma ray is released by some detector 24, and the remaining energy is released by another detector 24, so that the same gamma ray is sometimes detected by two or three or more detectors 24. Heretofore, such detection result of the scattered radiation has been simply abandoned. Hence, in the present embodiment, the detector scatter restoration process is performed, and a plurality of detection data caused by one gamma ray are integrated, so that the data of this gamma ray is reproduced for the utilization at the processing of the later stage. As a result, the detection sensitivity of the gamma ray of the nuclear medical diagnosis apparatus 100B is improved and the imaging time, that is, the detection time can be shortened. In addition, since the detectors 24 can be minutely arranged, the improvement of the resolution can be attained.

Figure 12:
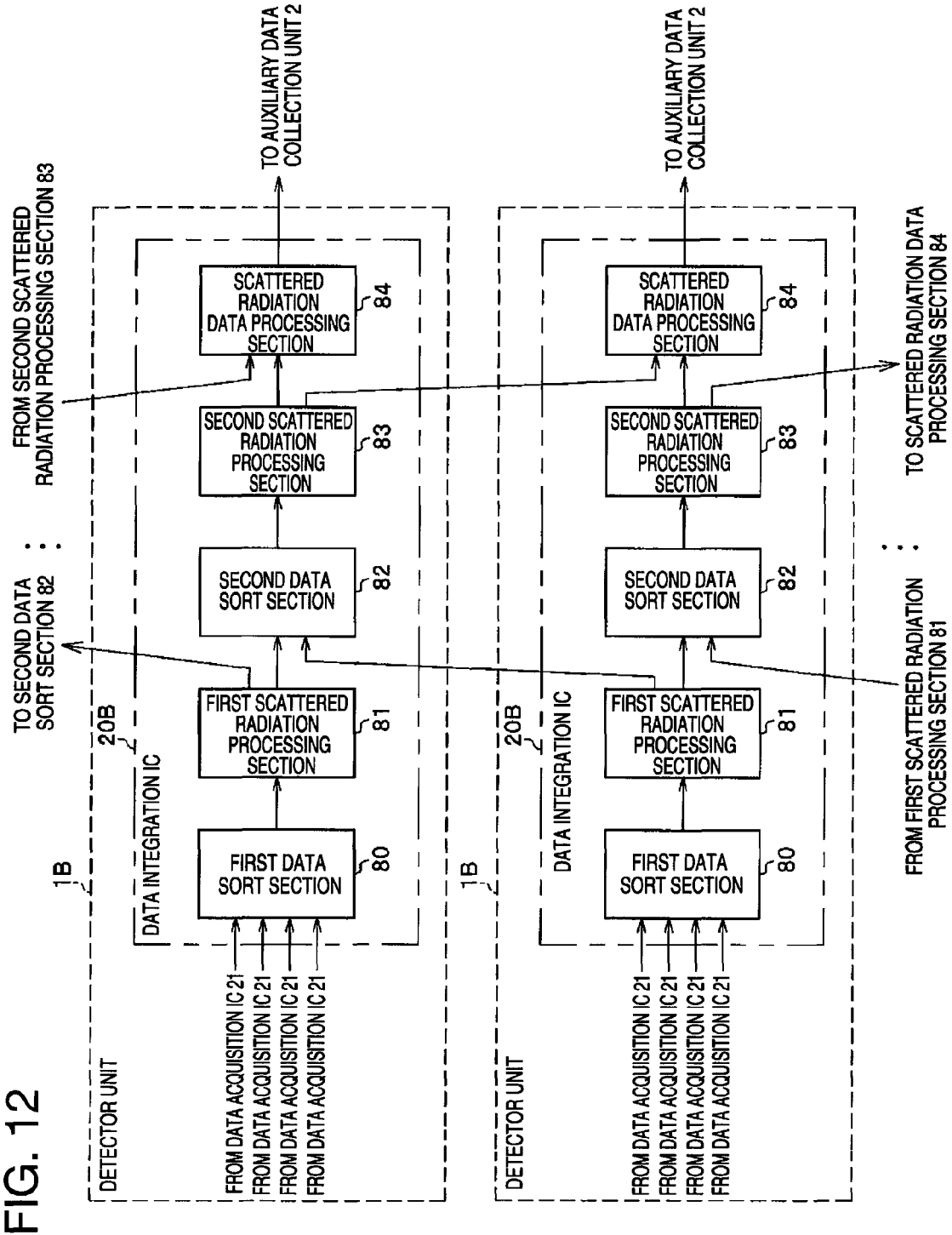
FIG. 12 is a configuration block diagram showing in details a detector unit.

As shown in FIG. 12, the detector unit 1B is provided with a data merge IC 20B in place of a data merge IC 20 in the detector unit 1.

The data merge IC 20B includes a function for performing the detector scatter restoration process, and is provided with a first data sort section 80, a first detector scatter restoration process section 81, a second data sort section 82, a second detector scatter restoration process section 83, and a scattered radiation data processing section 84. The first data sort section 80, the first detector scatter restoration process section 81, the second data sort section 82, the second detector scatter restoration process section 83, and the scattered radiation data processing section 84 are connected in this order. A plurality of data acquisition ICs 21 are connected to the first data sort section 80. In the adjacent first and second detector units 1B in the peripheral direction (peripheral direction of a through-bore section B) of the imaging apparatus having the detector unit 1B, the first detector scatter restoration process section 81 of the first detector unit 1B is connected to the second data sort section 82 of the second detector unit 1B. The second detector scatter restoration process section 83 of the second detector unit 1B is connected to the scattered radiation data processing section 84 of the first detector unit 1B. In other words, the second detector unit 1B for receiving the output of the first detector scatter restoration process section 81 of the first detector unit 1B and a third detector unit 1B for receiving the output of the second detector scatter restoration process section 83 of the first detector unit 1B are arranged so as to hold the first detector unit 1B in-between in the peripheral direction.

The first data sort section 80, apart from taking the output of a plurality of data acquisition ICs 21 as the input, has the same configuration as the data sort section 50 inside the data acquisition unit 3, and operates on the same principle. The first data sort section 80 arranges and merges the plurality of data packets inputted from the plurality of data acquisition ICs 21 in order of the detection time data, and outputs them to the first detector scatter restoration process section 81.

The first detector scatter restoration process section 81, as hereinafter described, performs a detector scatter restoration process for the inputted data packet, and has a function for integrating the plurality of the data packets caused by one gamma ray. One example of the detector scatter restoration process is disclosed in JP-A-2003-255048. The output of the first detector scatter restoration process section 81 is inputted to the second data sort section 82 inside this detector unit 1B and the second data sort section 82 inside the adjacent detector unit IB. A plurality of gamma rays caused by one gamma ray are not always detected by the detector unit 24 inside the same detector unit 1, but are often detected also by the detector 24 inside the adjacent detector unit 1B. Hence, after the detector scatter restoration process is performed by the first detector scatter restoration process section 81, the data packet is transferred also to the second data sort section 82 inside the adjacent detector unit 1B.

The first detector scatter restoration process section 81 of the first detector unit 1B outputs each data packet caused by the gamma ray detection signal of a part of the detectors 24 (preferably, in one area equally dividing the area inside the first detector unit 1B into two equal parts in the peripheral direction, all the detector units 24 positioned in the area close to the second detector unit 1B (one half of the detectors inside the first detector unit 1B)) positioned in the area close to the second detector unit 1B inside the first detector unit 1B to the second data sort section 82 of the second detector unit 1B.

The second data sort section 82, apart from being different in the input source of the data packet, has the same configuration as the first data sort section 80, and operates on the same principle. The second data sort section 82 of the second detector unit 1B, in a state in which each data packet inputted from the first detector scatter restoration process section 81 of the second detector unit 1B and the first detector scatter restoration process section 81 of the second detector unit 1B adjacent to that detector unit 1B in the peripheral direction, respectively is merged, arranges those data packets in order of the detection time data and outputs them to the second detector scatter restoration process section 83.

As described above, each second data sort section 82 outputs the data packets collected from the detector unit 1B to which it belongs and the detector unit 1B adjacent to this detector unit 1B in order of the detection time data (detection time). Here, the two data packet-columns inputted to the second data sort section 82 are already arranged in order of the detection time. Hence, only by selecting the data packets early in the detection time data from the head of the data packet column and merging them into one column, these data packets can be arranged in order of the detection time. As a result, the circuit scale can be reduced and high speed processing can be performed.

The second detector scatter restoration process section 83 has the same configuration as the first detector scatter restoration process section 81, and operates on the same principle. The second detector scatter restoration process section 83 performs the detector scatter restoration process by using the inputted data packet, and has a function for keeping track of the data packet based on the gamma ray detection signal of the detector 24 on which the gamma ray is incident in the first place from among the plurality of data packets caused by one gamma ray. The output of the second detector scatter restoration process section 83 is inputted to the scattered radiation data processing section 84 inside this detector unit 1B and the scattered radiation data processing section 84 inside the adjacent detector unit 1B. That is, the second detector scatter restoration process section 83, when the data packet after the detector scatter restoration process is the data packet of the detector unit 1B (for example, the second detector unit) to which it belongs, outputs that data packet to the scattered radiation data processing section 84 inside the detector unit (for example, the second detector unit) 1B to which it belongs, and when that data packet is the data packet of the adjacent detector unit (for example, the first detector unit) 1B, outputs that data packet to the scattered radiation data processing section 84 inside the adjacent detector unit (for example, the first detector unit) 1B, respectively.

The scattered radiation data processing section 84 has the same configuration and function as those of the first data sort section 80. The scattered radiation data processing section 84 performs the detector scatter restoration process based on the processing result at the second detector scatter restoration process section 83 of each data packet from the second detector scatter restoration process section 83 inside the detector unit (for example, the first detector unit) 1B to which it belongs and each data packet from the adjacent detector unit (for example, the second detector unit) 1B as well as each inputted data packets, and outputs the data packet based on the gamma ray detection signal of the detector unit 24 on which the gamma ray is incident in the first place from among the plurality of data packet caused by one gamma ray to the auxiliary data acquisition unit 2. The scattered radiation data processing section 84 arranges each packet data outputted to the auxiliary data acquisition unit 2 in order of the detection time data.

Figure 13:
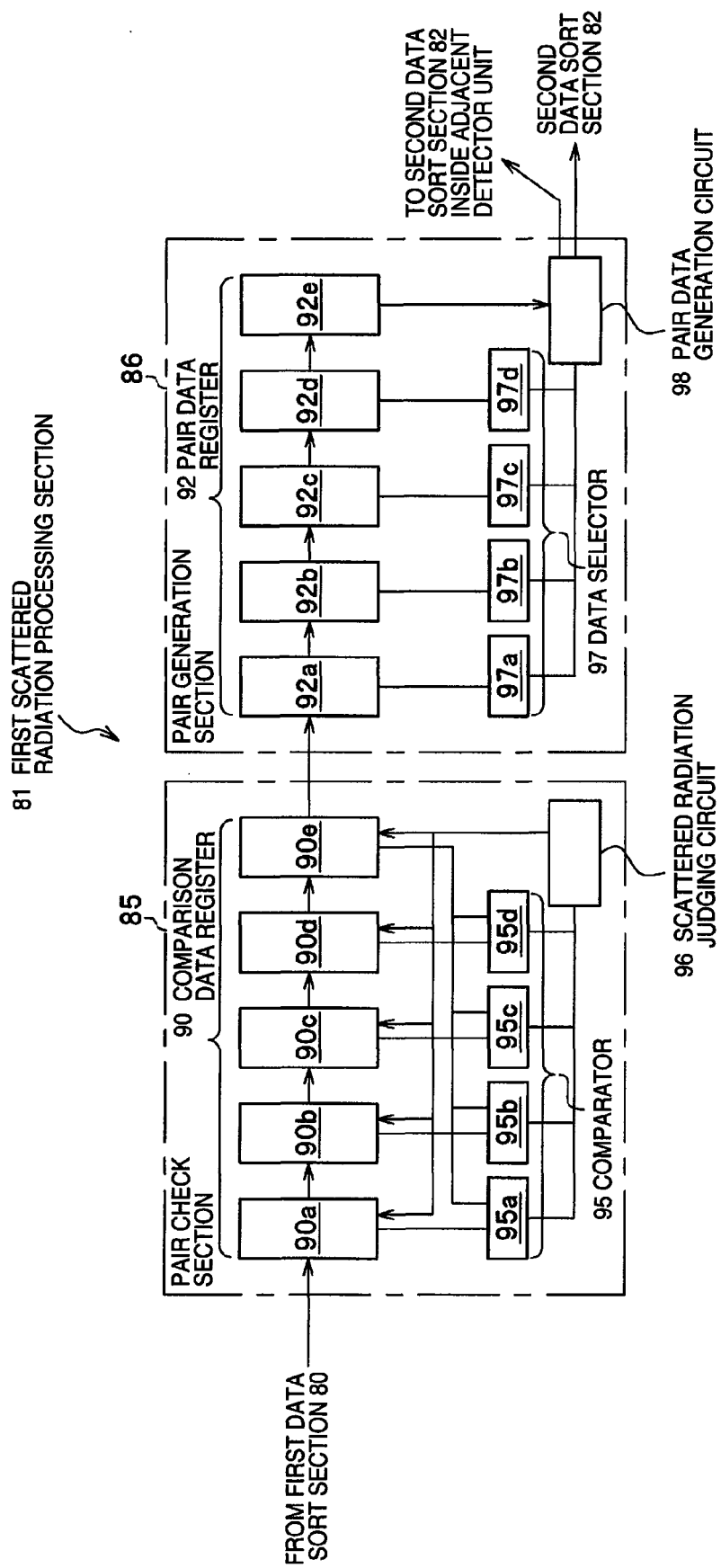
FIG. 13 is a configuration block diagram showing in details a first detector scatter restoration process section.

As shown in FIG. 13, the first detector scatter restoration process section 81 is provided with a pair check section 85 and a pair generation section 86. The configuration and the operation of the first detector scatter restoration process section 81 are pursuant to the coincidence detection section 51 described in the first embodiment, and the pair check section 85 is equivalent to the pair check section 52, and a pair generation section 86 is equivalent to the pair generation section 53. The pair check section 85 is provided with a comparison data register 90 including registers 90a to 90e, a comparator 95 including comparators 95a to 95d, and a scattered radiation judging circuit 96. The pair generation section 86 is provided with a pair data register 92 including registers 92a to 92e, a data selector 97 including selectors 97a to 97d, and a pair data generation circuit 98.

The data packet from the first data sort section 80 is inputted to a resistor 90a of a comparison data resistor 90. The comparison data resistor 90 is a shift register connecting registers 90a to 90e in series, and in synchronization with a clock, allows the data packet to shift in the forward direction (toward the resistor 90e) every one time slot.

The comparator 95 includes comparators 95a to 95d. The comparator 95 is connected to the registers 90a and 90e, and the comparator 95a is connected to the registers 90a and 90e, and likewise, the comparator 95b is connected to the registers 90b and 90e, the comparator 95c is connected to the registers 90c and 97e, and the comparator 95d is connected to the registers 90d and 90e. The scattered radiation judging circuit 96 has an input terminal connected to the comparators 95a to 95d, and an output terminal connected to the registers 90a to 90e, respectively.

Each of the comparators 95a to 95d receives each data packet stored in one corresponding register from among the registers 90a to 90d and each data packet stored in the register 90e, and judges whether or not these data packets are caused by one gamma ray. Specifically, each of the comparators 95a to 95d reads the identifier (means the detection position of the radiation) of each detector 24 and each detection time data from each data packets inside the corresponding register and the register 90e, and judges whether or not the two data packets are those inside the predetermined time window, and are in the detection position relationship possible as the scattered gamma ray. The comparators 95a to 95d judge whether or not a sum of the two energies included in the two data packets of the comparison objects is equal to the energy of the gamma ray emitted from the subject P. That energy of the gamma ray is 511 keV, which is an energy of the annihilation gamma ray caused by a pair annihilation of a positron-electron pair since a nuclear medical diagnosis apparatus 100B is a PET apparatus. When the nuclear medical diagnosis apparatus 100B is a SPECT apparatus, the energy is energy (for example, 140 keV) of the gamma ray emitted by a radioactive isotope labeling the drugs for SPECT.

The scattered radiation judging circuit 96 receives each of the judging results of the comparators 95a to 95d, and judges whether or not a pair of the data packets having satisfied the above described three judging conditions is one pair. The scattered radiation judging circuit 96, when the pair of the data packets is one pair, erects a scattered event flag (value is made 'valid') for each data packet stored in the corresponding one register and the register 90e from among the registers 90a to 90d, and when there are plural pairs of the pair (when plural events are detected), the scattered event flag is made 'invalid' (invalid flag is set). These processings are the same as the coincidence counting in the first embodiment.

The scattered radiation judging circuit 96 determines a total sum of energy regarding the data packet having satisfied the condition to the effect that the detection time is within a predetermined window and the detection positional relation ship is a scattered radiation, and when the energy is 511 keV, the scattered radiation judging circuit 96 judges that the corresponding plurality of data packets are the data packets of the scattered radiation caused by one gamma ray. The reason why is because, as described above, there is the possibility that one gamma ray is detected by three or more detectors 24. When such judgment is made, the scattered event flag is set on each of the corresponding data packets.

When the detector scatter restoration process is performed, the above described conditions of the scattered radiation are sometimes satisfied in a plurality of combinations. In the detector scatter restoration process, the data packets relating to these combinations are not made invalid, but the conditions of the combination are compared, and a distance between the detection positions and an interval of the detection time are taken into consideration, and three or more data packets are combined. The comparator 95 sets priorities by distance conditions and the detection time conditions, thereby attaching the flag, and the scattered judging circuit 96 selects the data packet of the combination highest in the priority, and the data packet relating to other combinations is disregarded.

The data packet from the pair check section 85 is inputted to the register 92a of the pair data register 92 the pair generation section 86. The pair data register 92 is a shift register connecting the registers 92a to 92e in series, and in synchronization with a clock, allows the data packet to shift in the forward direction (toward the resistor 92e) every one time slot. The data selector 97 includes the selector 97a to 97d. The selector 97a is connected to the register 92b, and the selector 97b to the register 92b, and the selector 97c to the register 92c, and the selector 97d to the register 92d, respectively. The selectors 97a to 97d are connected to the registers 92a to 92d, respectively, and at the same time, the selectors 97a to 97d are connected to the pair data generation circuit 98.

The pair data generation circuit 98 reads the scattered event flag of the data packet inputted to the register 92e. The pair data generation circuit 98, when the scattered event flag is set in the data packet, controls a data selector 97 (selectors 97a to 97d), and finds out the data packet used as a pair from the registers 70a to 70d. The pair data generation circuit 98, when the packet data used as a pair is present, outputs the data packet based on the gamma ray detection signal of the detector unit 24 on which the gamma ray is incident in the first place from among these data packets used as a pair as the data packet caused by one gamma ray. At this time, the data packet to be outputted includes those pieces of information on the representative data packet (data packet stored in the register 92e) with a total sum of energy relating to the data packet used as a pair taken as each information on the detection position and the detection time.

Figure 14:
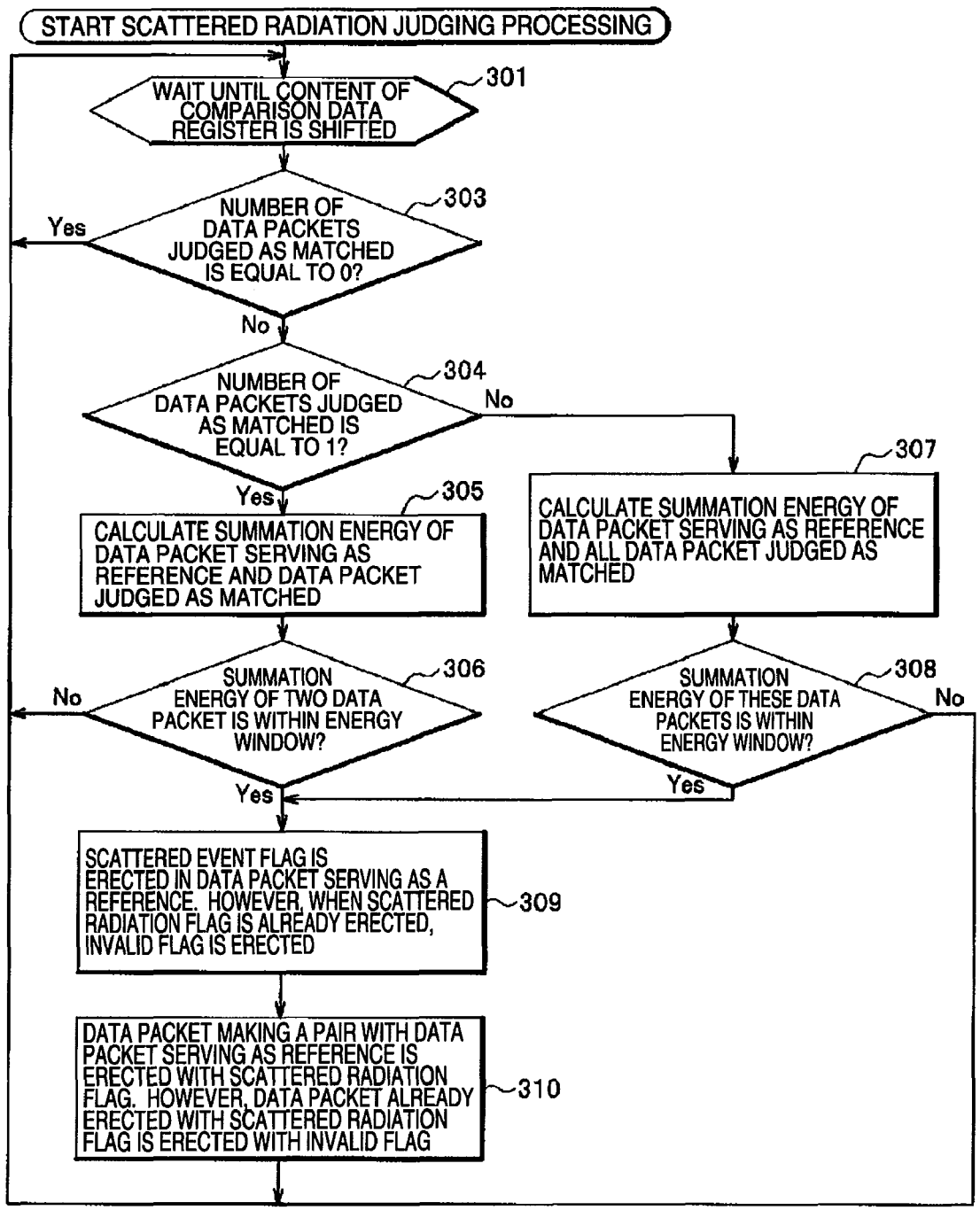
FIG. 14 is a flowchart showing a scattered radiation judging processing.

As described above, the second detector scatter restoration process section 83, apart from being different in an input source and an output destination, has the same configuration as the first detector scatter restoration process section 81, and performs the same detector scatter restoration process. Hence, with the first detector scatter restoration process section 81 cited as an example, and with reference to FIG. 14, the procedure of the scattered radiation judging processing executed in the scattered radiation judging circuit 96 will be described.

First, the scattered radiation judging circuit 96 waits until a new packet data is shifted to the register 90e in the comparison data register 90 (step 301). The scattered radiation judging circuit 96, after the new packet data is stored in the register 90e, executes each processing (scattered radiation judging processing) of steps 303 to 310. When the new packet data is stored in the register 90e, the scattered radiation judging circuit 96, first, based on the output information from the comparators 95a to 95d, judges whether or not the data packet judged as matched with the data packet (the data packet stored in the register 90e) serving as a reference is equal to 0 (step 303). When "Yes", the detector scatter restoration process is terminated, and the procedure proceeds to step 301, and repeats each of the subsequent processing. When the judgment is "No", the output information from the comparators 95a to 95d judges whether or not the data packet judged as matched is equal to one or more (step 303). When "No", a total sum of energy is determined (step 307) on all the data packet judged as matched with the data packet serving as a reference, and judges whether or not a total sum of energy relating to all the corresponding data packets is within the predetermined energy window (step 308). When this judgment is "No", the procedure returns to the processing of the step 301, and when "Yes", the processing of step 309 is performed.

When the judgment of step 304 is "Yes", with respect to the data packet serving as a reference and the data packet judged as matched, a total sum of energy is determined (step 305). It is judged whether or not a total sum of energy relating to all the corresponding data packets is within the predetermined energy window (step 306). When this judgment is "No", the procedure returns to the processing of step 301. When the judgment of step 306 is "Yes", the data packet serving as a reference is set with a reference scattered event flag. However, when the scattered event flag is already set, an invalid flag is set (the scattered event flag is made 'invalid') (step 309). The data packet serving as a reference and the data packet used as a pair are set with the scattered event flag. However, when the scattered event flag is already set, an invalid flag is set (the scattered event flag is made 'invalid') (step 310). After the completion of the processing of step 310, the processing of step 301 is executed.

Figure 15:
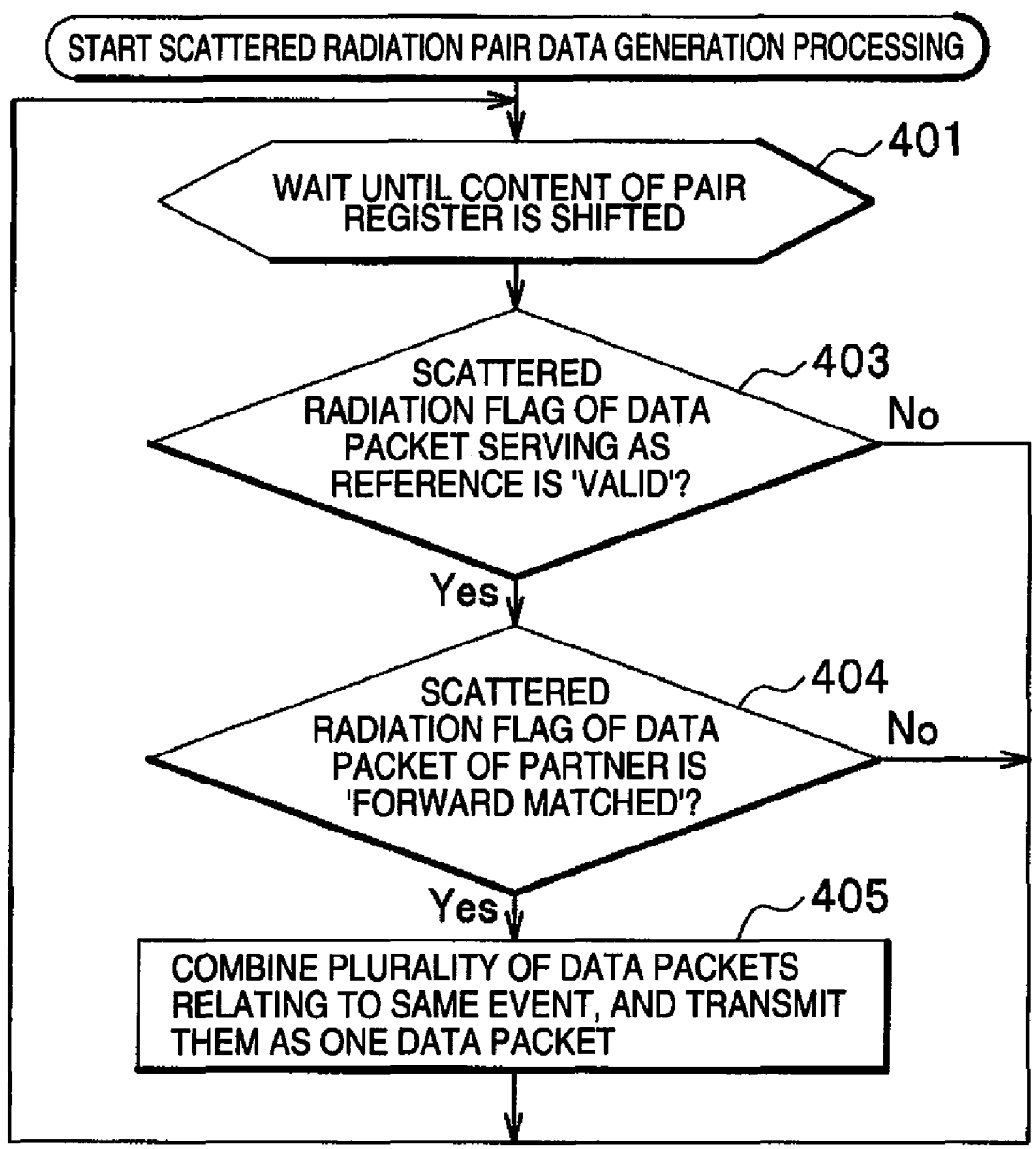
FIG. 15 is a flowchart showing a pair data generation processing in a detector scatter restoration process.

Referring to FIG. 15, the pair data generation processing executed by the pair data generation circuit 98 of a pair generation section 86 will be described. The second detector scatter restoration process section 83 also executes the same pair data generation processing. First, the pair data generation circuit 98 waits until a new packet data is shifted to the register 92e in the par data register 92 (step 401). Next, it is judged whether or not the scattered event flag of the data packet serving as a reference (the data packet stored in the register 92e) is 'valid' (step 403). When this judgment is "No", the processing of step 401 is performed. When the judgment is "Yes", it is judged whether or not the scattered event flag of the data packet of the partner side of the pair is 'forward-matched' (step 404). When this judgment is "No", the processing of step 401 is performed. When this judgment is "Yes", the data packet serving as a reference and the data packet (the data packet stored in the register other then the register 92e) of the partner are integrated, and the data packet serving as a reference is outputted as one piece of the data packet caused by one gamma ray (step 405). After that, each processing of steps 401 to 405 are repeated. The data packet to be outputted, as described above, includes a sum total of energy relating to the data packet used as a pair as energy information.

The scattered radiation judging processing (see FIG. 13) and the pair data generation processing (see FIG. 14) are executed in parallel during one clock for the plurality of data packets.

According to the nuclear medical diagnosis apparatus 100B of the present embodiment, the effects (a) and (b) obtained in the first embodiment can be obtained. The present embodiment can further obtain the following effects (e) and (f).

(e) Since the detector scatter restoration process is also performed by arranging the data packets in order of the detection time similarly to the coincidence counting processing, the number of data packets serving as the objects of the detector scatter restoration process is restricted, and the number of processing loads is reduced, and the speeding up of the operation and the reduction of the circuit scale can be attained, and at the same time, by adopting more complicated detector scatter restoration process logic, the detection data to lose can be further reduced, thereby making it possible also to improve the sensitivity of the nuclear medical diagnosis apparatus 100B.

(f) The present embodiment, in some detector unit and another detector unit adjacent to this detector unit, performs the detector scatter restoration process by the detection data obtained based on each gamma ray detection signal from a plurality of detectors 24, which are a part inside both detector units. Hence, in the case where the gamma ray incident on the detector 24 inside some detector unit is detected by the detector 24 of the adjacent detector unit due to scattering, when a total sum of energy of each gamma detection signal outputted from those detectors 24 is 511 keV, the detection data based on the gamma detection signal of the detector 24 on which the gamma ray is incident in the first place from among those two detector 24 can be utilized for the creation of a tomogram. Hence, the detection sensitivity of the gamma ray is improved much more, and the detection time can be further shortened.

Although the above description has been made on the embodiments, the present invention is not limited to those embodiments, and it is apparent to those skilled in the art that the invention can be variously modified and corrected within the scope of the invention and the accompanying claims.

It should be further understood by those skilled in the art that although the foregoing description has been made on embodiments of the invention, the invention is not limited thereto and various changes and modifications may be made without departing from the spirit of the invention and the scope of the appended claims.

DESCRIPTION OF REFERENCE NUMERALS 1, 1B Detector unit
3 Data acquisition unit (Merge means, Last stage merge means)
4 Collection console
10 Imaging apparatus
20 Data merge IC
21 Data acquisition IC
22 Analogue ASIC
24 Radiation detector
31 Pulse height measurement circuit
32 Time measurement circuit
33 Signal processing circuit (Data generation section)
34 Pulse height signal generation circuit
35 Timing signal generation circuit
37 ASIC control block (Data generation section)
47, 77, 97, 98 Data selector
48 Pair data generation circuit
50 Data sort section (Detection data output section)
51 Coincidence detection section (Coincidence counting device, Coincidence detection section, Delayed coincidence detection section)
52, 85 Pair check section
53, 86 Pair generation section
65 Unit data buffer (First detection data stream generation means, Second detection data stream generation means)
65a, 65b, 67a to 67c Buffer
66 Unit sort circuit (delayed detection data generation means)
70, 90 Comparison data register
70a to 70e, 72a to 72e, 90a to 90e, 92a to 92e Register
92e Register
72, 92 Pair data register
75, 75a to 75d, 95, 95a to 95d Comparator
76 Coincidence detection circuit
77a to 77d, 97a to 97d Selector
78 Pair data generation circuit
80 First data sort section
81 First detector scatter restoration process section (detector scatter restoration process section)
82 Second data sort section
83 Second detector scatter restoration process section (detector scatter restoration process section)
84 Scattered radiation data processing section
96 Scattered radiation judging circuit
100, 100B Nuclear medical diagnosis apparatus

The invention claimed is:

1. A nuclear medical diagnosis apparatus, comprising:
a plurality of radiation detectors arranged by surrounding around a bed supporting a subject and outputting a radiation detection signal according to the detection of the radiation;
a plurality of data generation sections for generating detection data including detection time data based on said radiation detection signal;
a detection data output section for outputting a predetermined number of said detection data outputted from a plurality of said data generation sections in order of the time of said detection time data included in the detection data; and a detector scatter restoring section for performing the detector scatter restoring based on a plurality of said detection data outputted in order of said time.

2. The nuclear medical diagnosis apparatus according to claim 1, wherein said detector scatter restoration process section judges whether or not said detection data serving as a reference from among a predetermined number of said detection data outputted from said detection data output section and each of another plurality of said detection data are a plurality of said detection data caused by said same radiation, and based on said judgment, a plurality of the detection data are merged.

3. A detector scatter restoring method of a nuclear medical diagnosis apparatus, wherein, based on a radiation detection signal outputted from a radiation detector having a plurality of radiation detectors arranged by surrounding a bed supporting a subject, a detection data including detection time data is generated, and a plurality of said detection data are outputted in order of the time of said detection time data included in said detection data, and the detector scatter restoring is performed based on a predetermined number of said detection data outputted in order of said time.

4. The detector scatter restoring method of the nuclear medical diagnosis apparatus according to claim 3, wherein it is judged whether or not said detection data serving as a reference from among a predetermined number of said detection data and another plurality of said detection data are a plurality of said detection data caused by same said radiation, respectively, and based on said judgment, said detection data is merged.

5. A nuclear medical diagnosis apparatus comprising:
a plurality of radiation detectors;
a plurality of data generation sections which generates detection data including detection time data for a radiation based on a detection signal outputted from each of the radiation detectors;
a first and second data sort section which orders and outputs the detection data according to an order of detection time data; and
a first and second scattered radiation processing section connected to the data sort section;
wherein the first data sort section is connected to the plurality of the data generation sections in the detector unit; and the second data sort section is connected to the detector unit and a first scattered radiation processing section of a neighboring detector unit.

* * * * *

UNITED STATES PATENT AND TRADEMARK OFFICE
CERTIFICATE OF CORRECTION

PATENT NO. : 7,807,974 B2
APPLICATION NO. : 12/034228
DATED : October 5, 2010
INVENTOR(S) : T. Ishitsu et al.

Page 1 of 1

It is certified that error appears in the above-identified patent and that said Letters Patent is hereby corrected as shown below:

ON THE TITLE PAGE

Please insert between Items (65) and (51):

--Related U.S. Application Data

(63)   Continuation of PCT application No. PCT/JP2007/053580, filed on February 27, 2007.

(30)   Foreign Application Priority Data

February 28, 2006   (JP).......................2006-054105--

IN THE SPECIFICATION

Column 1, line 1, insert:

--This is a continuation application of international application No. PCT/JP2007/053580, filed on February 27, 2007.--

Signed and Sealed this
Nineteenth Day of April, 2011

David J. Kappos
*Director of the United States Patent and Trademark Office*